(12) United States Patent
Bush et al.

(10) Patent No.: US 12,121,086 B2
(45) Date of Patent: Oct. 22, 2024

(54) MASK WITH ONE OR MORE SELF-SEALING PORTS AND SURGICAL KITS AND SYSTEMS ASSOCIATED THEREWITH

(71) Applicant: Medtronic Xomed, Inc., Jacksonville, FL (US)

(72) Inventors: Michael Bush, Jacksonville Beach, FL (US); Clint Lahey, Neptune Beach, FL (US); Craig M. Doherty, Tomball, TX (US); Jennifer Raines, Jacksonville, FL (US); Michael Geiger, Jacksonville, FL (US); Enrique A. Iturriaga, Jacksonville, FL (US); Scott Carpenter, Jacksonville, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 774 days.

(21) Appl. No.: 17/243,335

(22) Filed: Apr. 28, 2021

(65) Prior Publication Data
US 2021/0345699 A1    Nov. 11, 2021

Related U.S. Application Data

(60) Provisional application No. 63/041,679, filed on Jun. 19, 2020, provisional application No. 63/020,431, (Continued)

(51) Int. Cl.
*A41D 13/11* (2006.01)
*A61B 1/233* (2006.01)
*A61B 1/24* (2006.01)

(52) U.S. Cl.
CPC .......... *A41D 13/1146* (2013.01); *A61B 1/233* (2013.01); *A61B 1/24* (2013.01)

(58) Field of Classification Search
CPC .......... A61B 90/05; A61B 1/233; A61B 1/24; A61B 2017/345; A61B 17/3423;
(Continued)

(56) References Cited

U.S. PATENT DOCUMENTS

| 2,540,567 A | 2/1951 | Ray |
| 6,698,426 B1 | 3/2004 | Wright |

(Continued)

FOREIGN PATENT DOCUMENTS

| CN | 108310577 A | * | 7/2018 | ............. A61B 90/08 |
| WO | 2014124323 A1 | | 8/2014 | |
| WO | 2017131607 A1 | | 8/2017 | |

OTHER PUBLICATIONS

Machine Translation CN108310577A Accessed Feb. 10, 2024 (Year: 2024).*

(Continued)

*Primary Examiner* — Elliot S Ruddie
(74) *Attorney, Agent, or Firm* — Carter, DeLuca & Farrell LLP

(57) ABSTRACT

A patient mask including a body shaped to be placed over a face of a patient and configured to prevent the passage of viruses and/or particles therethrough and at least one port configured to receive an endoscope, a surgical instrument, or both and to conform to the shape of the surgical instrument such that the port prevents the passage of viruses and/or particles therethrough.

20 Claims, 13 Drawing Sheets

Related U.S. Application Data filed on May 5, 2020, provisional application No. 63/020,433, filed on May 5, 2020, provisional application No. 63/020,435, filed on May 5, 2020.

(58) Field of Classification Search
CPC ... A61B 90/40; A62B 23/02–025; A62B 9/00; A62B 18/08; A62B 7/10; A62B 7/02; A62B 18/086; A41D 13/11; A41D 13/1146; A61M 16/0816; A61M 16/105–107; A61M 2202/0208; A61M 2039/0626; A61M 2039/0633; A61M 2202/20; A61M 2202/203; A61M 2202/206; A61M 2205/053; A61M 2205/7509; A61M 2205/7518; A61M 2209/06; A61M 2210/0618; A61M 2210/0625; A61M 16/0093; A61M 16/06; A61M 16/1055; A61M 16/1065; A61M 16/208; A61M 39/02; A61M 39/22; A61M 39/06; A61M 16/0683; B01D 39/1623; B01D 2239/0241; B01D 2239/065; A61L 9/20; A61L 2209/14
USPC ............ 128/205.25, 202.28, 205.13, 205.29, 128/206.16, 206.17, 206.21, 206.28, 128/206.29

See application file for complete search history.

(56) References Cited

U.S. PATENT DOCUMENTS

| | | | |
|---|---|---|---|
| 6,792,943 B2 | 9/2004 | Kumar et al. | |
| 6,988,500 B1 | 1/2006 | Cox | |
| 7,290,545 B2 | 11/2007 | Kleman et al. | |
| 7,360,538 B2 | 4/2008 | Flynn | |
| 8,291,905 B2 | 10/2012 | Moenning, Jr. | |
| 8,479,737 B2 | 7/2013 | Moenning, Jr. | |
| 8,539,953 B2 | 9/2013 | Moenning, Jr. | |
| 9,126,004 B2 | 9/2015 | Flynn | |
| 9,320,923 B2 | 4/2016 | Koehler | |
| 9,468,782 B2 | 10/2016 | Koehler | |
| 9,629,401 B2 | 4/2017 | Malki | |
| 9,656,037 B2 | 5/2017 | Guyette | |
| 10,188,814 B2 | 1/2019 | Moenning, Jr. | |
| 10,834,978 B1 | 11/2020 | Yelken | |
| 10,849,375 B1 | 12/2020 | Bowen et al. | |
| 10,918,142 B2 | 2/2021 | Loughran | |
| 10,966,471 B1 | 4/2021 | Yelken | |
| 11,000,655 B1* | 5/2021 | Fox | A61M 16/0616 |
| 11,020,557 B1* | 6/2021 | Lehman | A61B 5/082 |
| 11,033,060 B1 | 6/2021 | Yelken | |
| 11,071,336 B2 | 7/2021 | Belousov | |
| 2004/0177851 A1 | 9/2004 | Acosta | |
| 2006/0201511 A1* | 9/2006 | Freriks | A62B 17/04 128/206.13 |
| 2013/0092173 A1 | 4/2013 | Alexander et al. | |
| 2013/0172768 A1* | 7/2013 | Lehman | A61M 16/06 128/205.25 |
| 2017/0007795 A1 | 1/2017 | Pedro et al. | |
| 2019/0038863 A1* | 2/2019 | Chang | A61M 16/208 |
| 2020/0289533 A1 | 9/2020 | Wei | |
| 2021/0145089 A1 | 5/2021 | Hassan | |

OTHER PUBLICATIONS

PCT Search Report and Written Opinion issued in PCT Application No. PCT/US2021/029715 dated Aug. 15, 2021, 14 pages.

* cited by examiner

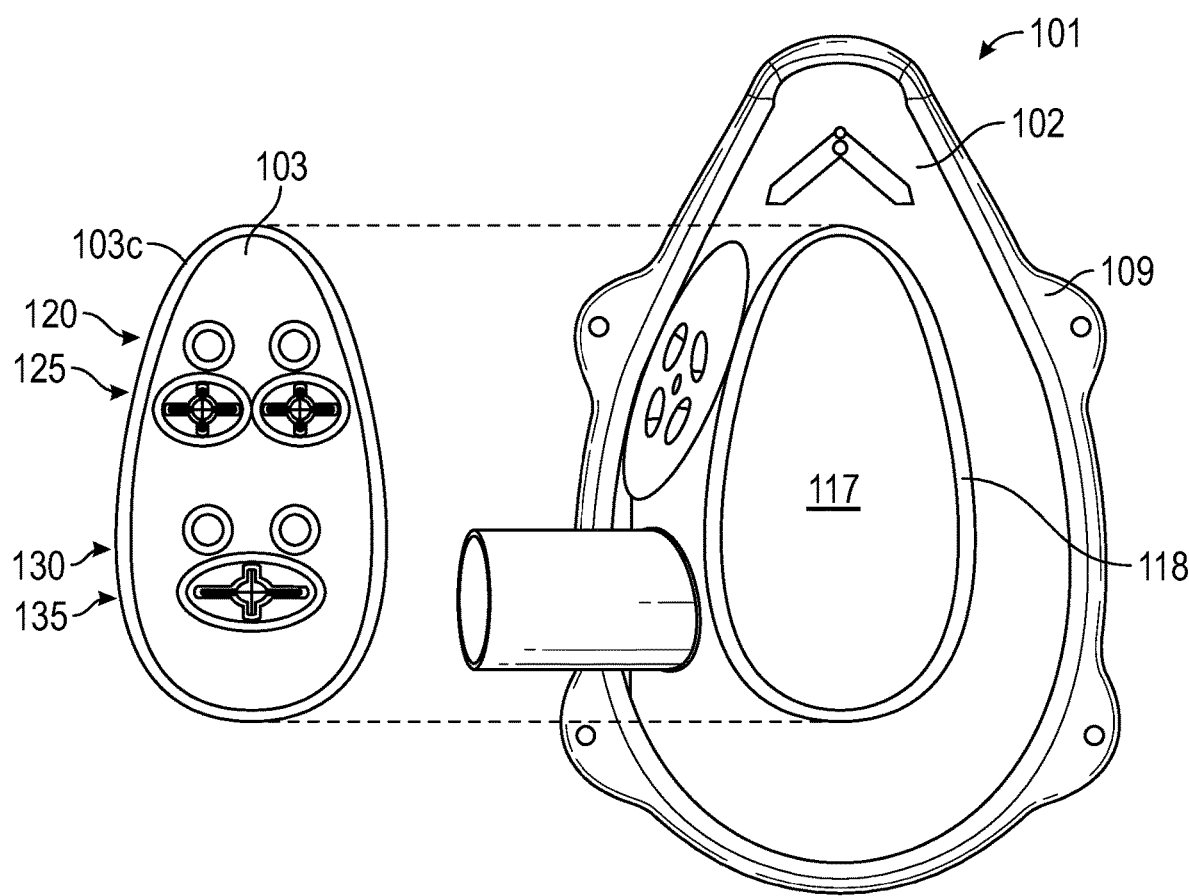
FIG. 5A
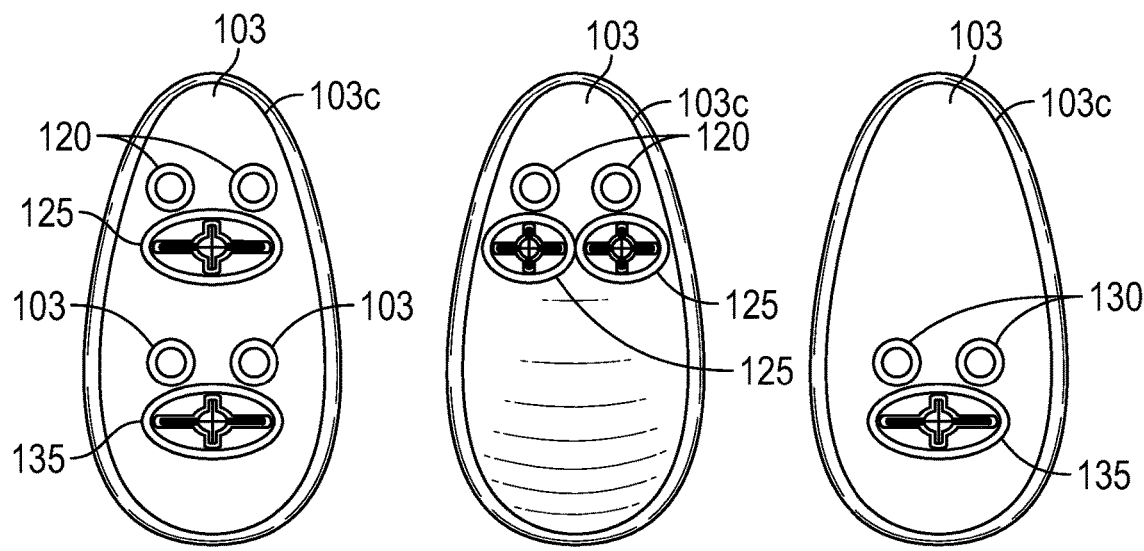
FIG. 5B  FIG. 5C  FIG. 5D

MASK WITH ONE OR MORE SELF-SEALING PORTS AND SURGICAL KITS AND SYSTEMS ASSOCIATED THEREWITH

CROSS-REFERENCE TO RELATED APPLICATIONS

This application claims benefit of and priority to U.S. Provisional Application Ser. Nos. 63/020,431, 63/020,433, and 63/020,435, each filed May 5, 2020, the disclosure of each of the above-identified applications is hereby incorporated by reference in its entirety.

BACKGROUND

Technical Field

This disclosure relates to a mask configured to be worn by a patient and including one or more self-sealing access ports. More particularly the disclosure is directed to a patient mask configured to provide access to at least one, if not both, of a nose or mouth of a patient while also preventing the transmission of a harmful particle, virus, and/or bacteria by exhaled air contaminated with such particle, virus, and/or bacteria from endangering a clinician.

Related Art

In the past century three pandemics of Influenza have been witnessed, of which the "Spanish flu" of 1918 was the largest pandemic of any infectious disease known to medical science. The three strains which caused these pandemics belong to group A of the influenza virus and, unlike the other two groups (B and C), this group infects a vast variety of animals (poultry, swine, horses, humans and other mammals). Influenza A virus continue to cause global problems, both economically and medically. The avian Influenza A H5N1 virus, which first demonstrated its ability to infect birds in China in 1997 and has since spread to other countries in South East Asia, Europe, and Africa. Its ability to cause severe disease in birds was documented by the World Health Organization during a mild outbreak in South East Asian birds during 2003-2004. H5N1 mutates rapidly and is highly pathogenic. Its co-existence with other avian influenza virus increases the likelihood of concurrent infections in birds. Such events would provide the 'mixing vessel' for the emergence of a novel subtype with sufficient avian genes to be easily transmitted between avian species, which would mark the start of an influenza epidemic. The current COVID-19 pandemic has again heightened the public awareness and the need for risk mitigation systems and methods related to all of these viruses.

Much has been done to control and prevent another pandemic from occurring with many anti-influenza products (vaccines and treatments) currently on the market. Presently, Amantadine is the principal antiviral compound against Influenza infections, but its activity is restricted to Influenza A virus. Anti-neuraminidase inhibitors, such as Zanamivir (Relenza) and Oseltamivir (Tamiflu), are a new class of antiviral agents licensed for use in the treatment of both Influenza A and B infections. The role of these antivirals in a pandemic may be limited due to the time and cost involved in production and the current limited supply. With the recent news of a probable H5N1 pandemic the need to prevent any opportunities of transmission of the virus between avian species has risen.

The inhalation of air contaminated by harmful virus and/or other micro-organisms is a common route for infection of human beings, particularly health workers and others caused to work with infected humans or animals. Air exhaled by infected patients is a source of contamination. At the present time, the risk of infection by the COVID-19 virus is of particular concern.

Masks, the ubiquitous form of personal protective equipment (PPE) incorporating a suitable filter material have been deployed to present a barrier to prevent transmission of the virus. Air filters believed to remove such virus and/or other micro-organisms are known. One type of such a filter comprises a fibrous or particulate substrate on which is deposited, upon the surface and/or into the bulk of such fibers or particles, a substance which captures and/or neutralizes virus and/or other micro-organisms of concern.

While the filter materials themselves have been studied, these are typically deployed on patients, who are seen by healthcare provides in a doctor's office, clinic, or emergency room. But the masks, do not provide access to the patient to enable diagnosis and treatment. Indeed, very little technology has been developed to enable clinical care of such patients, particularly ear, nose, and throat (ENT) patients, and yet provide the appropriate protection to the caregiver. As will be appreciated, covering the nose and mouth of a patient presents a barrier to use of endoscopes and the deployment of surgical instruments through these natural orifices.

SUMMARY

The present disclosure describes a patient mask including a body shaped to cover at least a portion of a face of a patient creating a space therebetween, i.e., between the patient's face and the inner surface of the mask body. The mask body including at least a nasal portion configured to cover a nasal area of the patient, a perioral portion configured to cover a perioral area of the patient, and at least one filter passage attached to the body. The nasal and perioral portions of the body being adjacent each other. The at least one filter passage configured to filter air passing therethrough.

The nasal portion of the body may include at least one nasal endoscope port configured to receive an endoscope therethrough. The at least one nasal endoscope port being substantially self-sealing with or without an endoscope positioned therethrough. The at least one nasal endoscope port being positioned on a first upper part of the nasal portion of the body. In some embodiments, the nasal portion includes two nasal endoscope ports, each nasal endoscope port configured to generally align with a nostril of a typical patient.

The nasal portion of the body may further include at least one nasal instrument port configured to receive a surgical instrument therethrough. The at least one nasal instrument port being substantially self-sealing with or without a surgical instrument positioned therethrough. The at least one nasal instrument port being positioned on a second part of the nasal portion of the body different from the nasal endoscope ports. In some embodiments, the nasal portion includes two nasal instrument ports, each instrument port centered on the same longitudinal axis as a nasal endoscope port.

In some embodiments, the perioral portion of the patient mask body may further include at least one perioral endoscope port configured to receive an endoscope therethrough, at least one perioral instrument port configured to receive a surgical instrument therethrough, or both. The at least one perioral endoscope port being substantially self-sealing with or without an endoscope positioned therethrough. The at least one perioral endoscope port positioned on a first part of the perioral portion of the body. In some embodiments, the perioral portion of the body may include two perioral endoscope ports. The two perioral endoscope ports may be the same size as the nasal endoscope port(s).

The at least one perioral instrument port being substantially self-sealing with or without an instrument positioned therethrough. The at least one perioral instrument port positioned on a second part of the perioral portion of the body. In some embodiments, the perioral portion of the body may include only one perioral instrument port. The one perioral instrument port may be larger in size than the nasal instrument port(s).

In some embodiments, the body includes a first one-way filter passage configured to filter air passing therethrough from the space inside the body of the mask to outside the body of the mask. In such embodiments, the body may further include an umbrella valve configured as an inlet of air into the mask from outside the mask when a patient inhales. Alternatively, in such embodiments, instead of an umbrella valve, the inlet may include a second on-way filer passage configured to filter air passing therethrough from outside the mask into the space inside the mask.

In some embodiments, the at least one filter passage includes a two-way filter passage configured to filter air passing therethrough in a first direction from the space inside the body of the mask to outside the body of the mask and further configured to filter air passing therethrough in a second direction from outside the body of the mask into the space inside the body of the mask.

The masks described herein may include at least one strap secured to a portion of the body. The at least one strap configured to secure the mask to the face of the patient.

The masks described herein may further include a nose-bridge configured to improve the body's ability to confirm to the contour of a bridge of a nose of the patient when positioned thereon.

The patient mask body may be made of one-piece or multi-piece construction.

In some embodiments, the present disclosure also describes a patient mask including a body having a central face surrounded by an outer sidewall. The outer sidewall being configured to space the central face of the body from a face of a patient. The central face includes a nasal portion configured to cover a nasal area of the patient, a perioral portion configured to cover a perioral area of the patient, and at least one filter passage attached to the outer sidewall portion of the body. The nasal and perioral portions of the body being adjacent each other on the central face. The at least one filter passage configured to filter air passing therethrough.

The nasal portion of the central face may include at least one nasal endoscope port configured to receive an endoscope therethrough. The at least one nasal endoscope port being substantially self-sealing with or without an endoscope positioned therethrough. The at least one nasal endoscope port being positioned on a first upper part of the nasal portion of the central face. In some embodiments, the nasal portion includes two nasal endoscope ports, each nasal endoscope port configured to generally align with a nostril of a typical patient.

The nasal portion of the central face may further include at least one nasal instrument port configured to receive a surgical instrument therethrough. The at least one nasal instrument port being substantially self-sealing with or without a surgical instrument positioned therethrough. The at least one nasal instrument port being positioned on a second part of the nasal portion of the central face different from the nasal endoscope ports. In some embodiments, the nasal portion includes two nasal instrument ports, each instrument port centered on the same longitudinal axis as a nasal endoscope port.

In some embodiments, the perioral portion of the central face may further include at least one perioral endoscope port configured to receive an endoscope therethrough, at least one perioral instrument port configured to receive a surgical instrument therethrough, or both. The at least one perioral endoscope port being substantially self-sealing with or without an endoscope positioned therethrough. The at least one perioral endoscope port positioned on a first part of the perioral portion of the central face. In some embodiments, the perioral portion of the central face may include two perioral endoscope ports. The two perioral endoscope ports may be the same size as the nasal endoscope port(s).

The at least one perioral instrument port being substantially self-sealing with or without an instrument positioned therethrough. The at least one perioral instrument port positioned on a second part of the perioral portion of the central face. In some embodiments, the perioral portion of the central face may include only one perioral instrument port. The one perioral instrument port may be larger in size than the nasal instrument port(s).

In some embodiments, the outer sidewall includes a first one-way filter passage configured to filter air passing therethrough from the space inside the body of the mask to outside the body of the mask. In such embodiments, the outer sidewall may further include an umbrella valve configured as an inlet of air into the mask from outside the mask when a patient inhales. Alternatively, in such embodiments, instead of an umbrella valve, the inlet may include a second on-way filer passage configured to filter air passing therethrough from outside the mask into the space inside the mask.

In some embodiments, the at least one filter passage includes a two-way filter passage configured to filter air passing therethrough in a first direction from the space inside the body of the mask to outside the body of the mask and further configured to filter air passing therethrough in a second direction from outside the body of the mask into the space inside the body of the mask.

The masks and/or mask bodies described herein may also be configured to be used with separate, free-standing systems configured to purify and/or sterilize at least the exhaled air of the patient.

Surgical kits including any combination of the various patient masks, mask bodies, ports of access, and/or filters described herein are also provided.

BRIEF DESCRIPTION OF THE DRAWINGS

Various aspects of the present disclosure are described herein below with reference to the drawings, which are incorporated in and constitute a part of this specification, wherein:

FIG. 5A is a top view of multipiece body of a patient mask in accordance with at least one embodiment herein;

FIGS. 5B-5D are top views of various central face designs in accordance with at least one embodiment herein;

DETAILED DESCRIPTION

The present disclosure is directed to surgical masks configured to be worn by a patient, i.e., patient mask, and filtering systems configured to work therewith. In particular, the present disclosure is directed to a patient mask configured to cover at least a nasal area of a patient's face, and more particularly at least a nasal and perioral area of a patient's face. When properly placed on and/or strapped to the patient's face, the masks described herein are configured to form an airtight barrier around the nose and/or mouth of the patient while also providing access therethrough to the patient's natural orifices, such as the nose and/or mouth while reducing and/or eliminating the likelihood of a clinician from becoming exposed to and/or infected by a virus or other particulate matter that may be expelled by the patient during a procedure.

Figure 1:
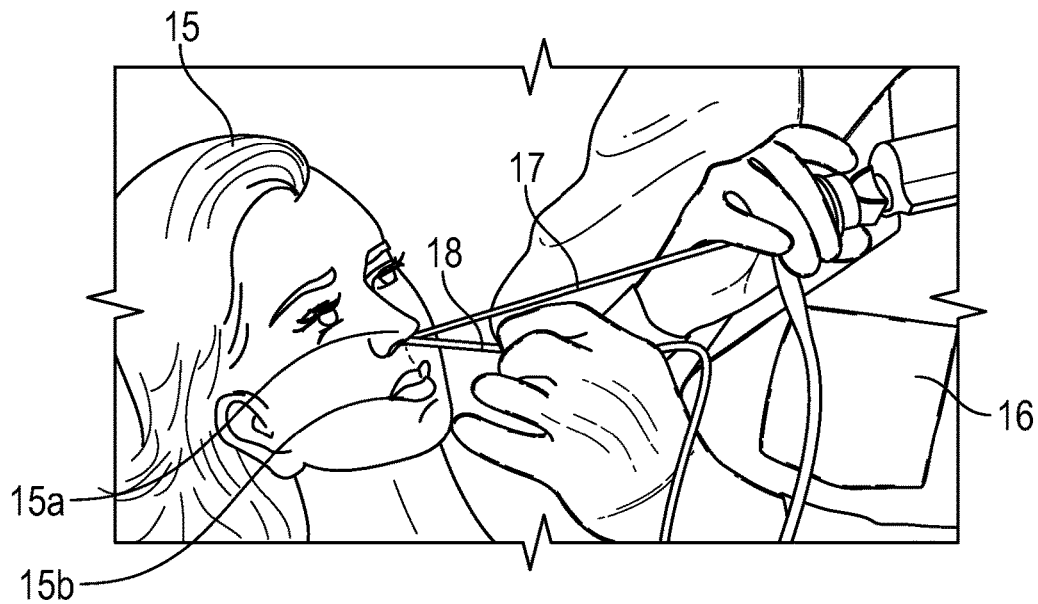
FIG. 1 shows a patient with an endoscope and another surgical instrument inserted into one or more nares of the patient's nose during a typical ENT procedure.

FIG. 1 depicts a generally common manner in which a patient 15 suffering from an ailment, such as an ear, nose and/or throat (ENT) ailment, may be examined, diagnosed, treated, tested, and/or biopsied. The patient 15 of FIG. 1 appears ambulatory and generally awake during the depicted office procedure performed generally in the nasal area 15a of the patient 15 while the perioral area 15b of the patient 15 remains uninvolved with the depicted procedure. Specifically, an endoscope 17 and another surgical instrument 18 are shown inserted into one or more nares of the patient's nose.

As will be appreciated, such close proximity of the clinician 16 and the patient 15 during a typical procedure is well within current 6-foot social distancing standards that are a first line of defense in preventing the spread of a virus, such as influenza viruses (e.g., the flu), coronaviruses (e.g., the COVID-19 virus, MERS, SARS), and/or rhinoviruses (including those associated with the common cold), as well as the spread of a bacteria, such as *streptococcus* bacteria (e.g., Strep Throat) and/or meningococcus bacteria (e.g., meningitis). Thus, there is a need for the patient masks of the present disclosure to form a seal and/or barrier between patient 15 and clinician 16 while maintaining the clinician's ability access to the patient's natural orifice's without compromising the seal and/or barrier therebetween. The present disclosure provides a system and method that is useable with the masks described herein for patients that may be awake and/or ambulatory patients, as well as for sedated or anesthetized patients to limit the spread of viruses or other pathogens from the patient to the clinician.

Figure 2:
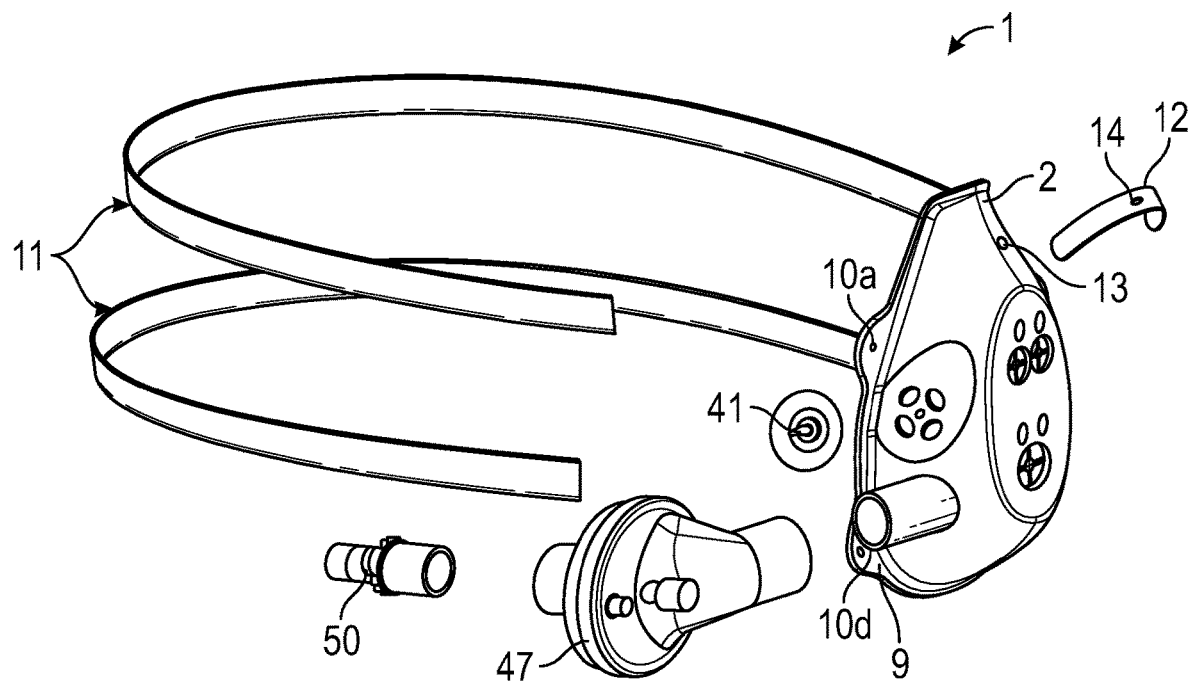
FIG. 2 shows a perspective view of a patient mask configured for receipt of at least one or more endoscopes and/or surgical instruments in accordance with the disclosure.

FIG. 2 depicts a patient mask 1 of the present disclosure including a body 2 shaped to cover at least a portion of a face of a patient (not shown) and one or more, e.g., two, straps 11 configured to positioned around and/or over a patient's head to secure the body 2 of the mask 1 on the patient's face. In some embodiments, the body 2 of the mask 1 is configured to cover both the nasal area 15a and perioral area 15b of a patient. The mask 1 may also include a nose-bridge 12.

As depicted in FIG. 2, the body 2 may include an outer ledge 9 extending therefrom. The outer ledge 9 includes two or more strap openings 10a-d configured to secure the one or more straps 11 to the body 2. In some embodiments, opposite ends of the strap(s) 11 may be tied to the body 2 of the mask 1 via strap openings 10. The straps may be made of any suitable material known to those of ordinary skill.

As further depicted in FIG. 2, in some embodiments, a separate filter 47 may be secured to a portion of the body 2 of the mask 1. The separate filter 47 may be a one-way filter or a two-way filter. An adapter 50 is also depicted, the adapter 50 configured to connect a free end 47b of the filter 47 to an endotracheal tube or a suction device (not shown).

FIGS. 3A-3E depict various views of the body 2 of the patient mask 1 of FIG. 2. The one or more straps 11, the filter 47, and the adapter 50 are not shown for clarity purposes. In some embodiments, the body 2 may include a generally central face 3 surrounded by an outer sidewall 4 configured to create a space 5 inside the mask 1 (and/or body 2) between the central face 3 of the mask 1 and a patient's face when properly positioned and/or strapped thereon.

The outer sidewall 4 extends between a first peripheral sidewall edge 4a and a second peripheral sidewall edge 4b opposite the first peripheral sidewall edge 4a. The first peripheral sidewall edge 4a may extend from an area near or at an outer edge 3a of the central face 3. The second peripheral sidewall edge 4b may be configured to form a seal between a patient's face and the body 2 (and/or mask 1). The outer sidewall 4 may extend from the central face 3 to a patient's face in a curved or linear manner.

The central face 3 includes an upper nasal portion 7 configured to cover a nasal area of a patient's face and a lower perioral portion 8 configured to cover a perioral area of a patient's face. The upper nasal portion 7 of the central face 3 may include at least one nasal endoscope port 20 on a first part thereof and/or at least one nasal instrument port 25 on a second part thereof, the second part being different than the first part. The nasal endoscope port 20 is configured to receive an endoscope therethrough, and particularly an endoscope configured to be positioned within a nasal cavity of a patient. The nasal endoscope port 20 is also substantially self-sealing. The nasal instrument port 25 is configured to receive a surgical instrument therethrough, and particularly a surgical instrument configured to be positioned within a nasal cavity of a patient. The nasal instrument port 25 is also substantially self-sealing.

By self-sealing, each of the sealed ports (e.g., endoscope ports and instrument ports) are configured to maintain a seal prior, during, and after an endoscope or instrument is positioned therethrough.

Figure 3A:
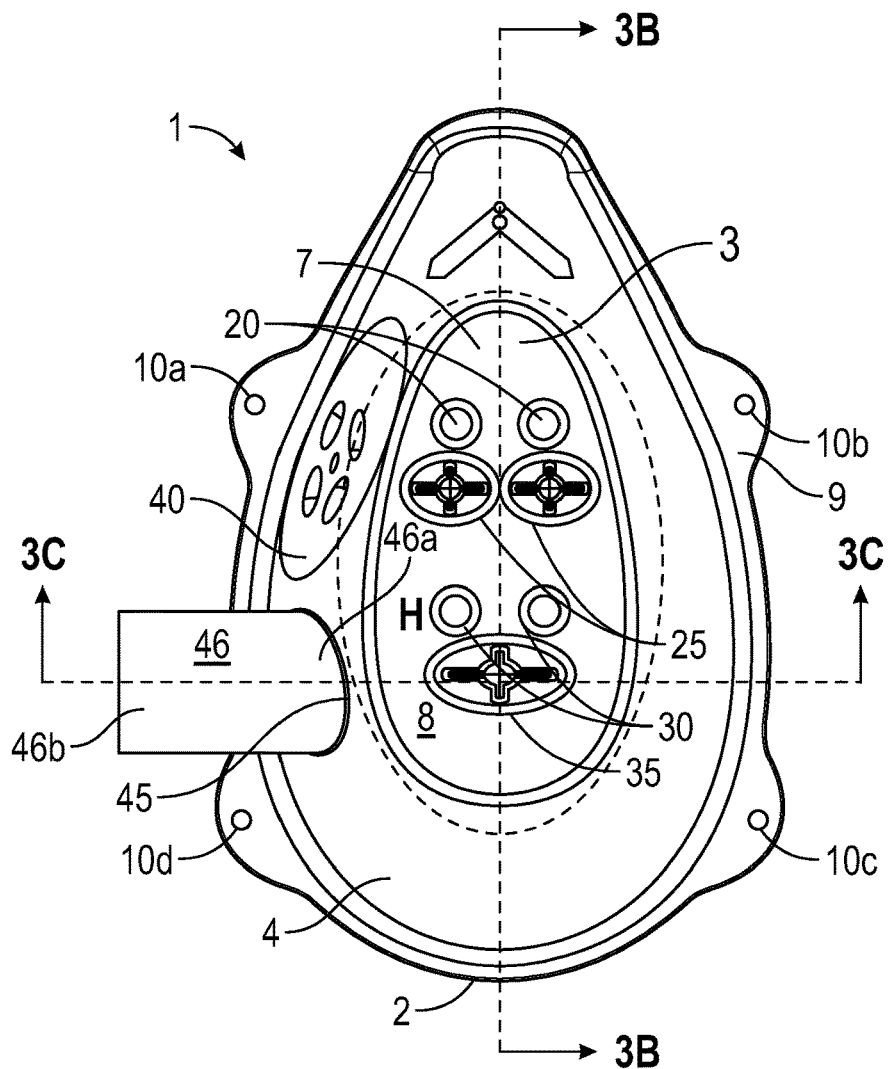
FIG. 3A is a top view of the body of the mask of FIG. 2 in accordance with at least one embodiment described herein.
Figure 3B:
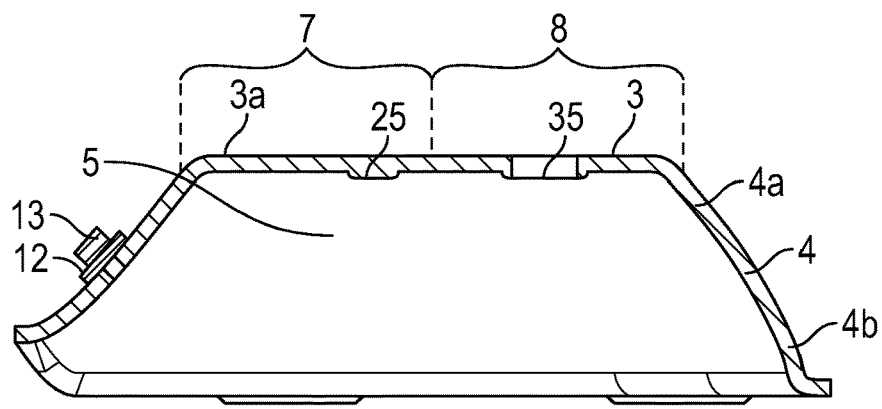
FIG. 3B is a cross-sectional side view of the body of the mask of FIG. 2 in accordance with at least one embodiment described herein.

As shown in FIG. 3A, in some embodiments, the upper nasal portion 7 of the central face 3 may include two nasal endoscope ports 20, two nasal instrument ports 25, or both. As further shown in FIG. 3A, in some embodiments, the upper nasal portion 7 of the central face 3 may include two nasal endoscope ports 20 positioned on top of and/or centered on top of two nasal instrument ports 25.

As further shown in FIG. 3A, the lower perioral portion 8 of the central face 3 may further include at least one perioral endoscope port 30 on a first part thereof and/or at least one perioral instrument port 35 on a second part thereof, the second part being different than the first part. The perioral endoscope port 30 is configured to receive an endoscope therethrough, and particularly, an endoscope configured to be positioned within a nasal or oral cavity of a patient. The perioral endoscope port 30 is also substantially self-sealing. The perioral instrument port 35 is configured to receive a surgical instrument therethrough, and particularly a surgical instrument configured to be positioned within a nasal or oral cavity of a patient. The perioral instrument port 35 is also substantially self-sealing.

As further shown in FIG. 3A, in some embodiments, the lower nasal portion 8 of the central face 3 may include two perioral endoscope ports 30, one perioral instrument port 35, or both. As still further shown in FIG. 3A, in some embodiments, the lower perioral portion 8 of the central face 3 may include two perioral endoscope ports 30 positioned on top of one perioral instrument port 35.

The mask 1 (and/or body 2) may further include an inlet 40 and/or an outlet 45. The inlet 40 is configured to allow air to pass therethrough from outside the mask 1 (and/or body 2) into the space 5 inside the mask 1 (and/or body 2). The outlet 45 is configured to allow air to pass therethrough from the space 5 inside the mask 1 (and/or body 2) to the outside of the mask 1 (and/or body 2). In some embodiments, at least one, if not both, the inlet 40 and the outlet 45 include a filter configured to purify the air passing therethrough.

As shown in FIGS. 3A, 3C, 3D, and 3E, in some embodiments, the inlet 40 and/or the outlet 45 may be positioned on and/or defined through the outer sidewall 4. In some embodiments, the inlet 40 and the outlet 45 may be located on the outer sidewall 4 on the same side of the body 2 relative to a longitudinal axis A1 of the body 2 (and/or central face 3). In some embodiments, the inlet 40 and the outlet 45 may be located on the outer sidewall 4 on opposite sides of the body 2 relative to the central face 3 (FIG._).

As further shown in FIGS. 3A, 3C-3F, in some embodiments, the inlet 40 may be an umbrella valve 41 configured to transition between an open position during inhalation of the patient and a closed position during exhalation of the patient. In the open position, air is allowed to pass through the valve 41 from outside the mask 1 (and/or body 2) into the space 5 inside the mask 1 (and/or body 2). In the closed position, air is prevented from passing through the valve 41.

Figure 3C:
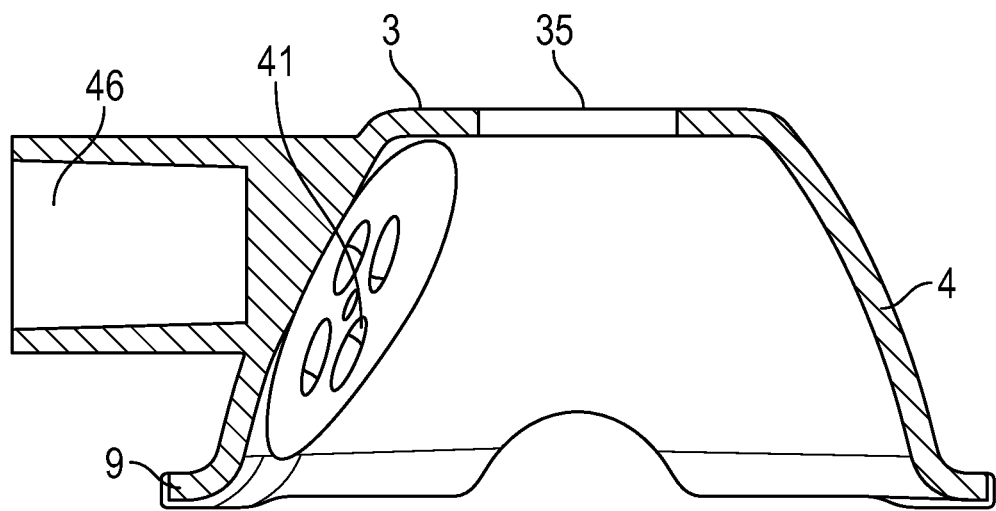
FIG. 3C is a cross-sectional end view of the body of the mask of FIG. 2 in accordance with at least one embodiment described herein.
Figure 3D:
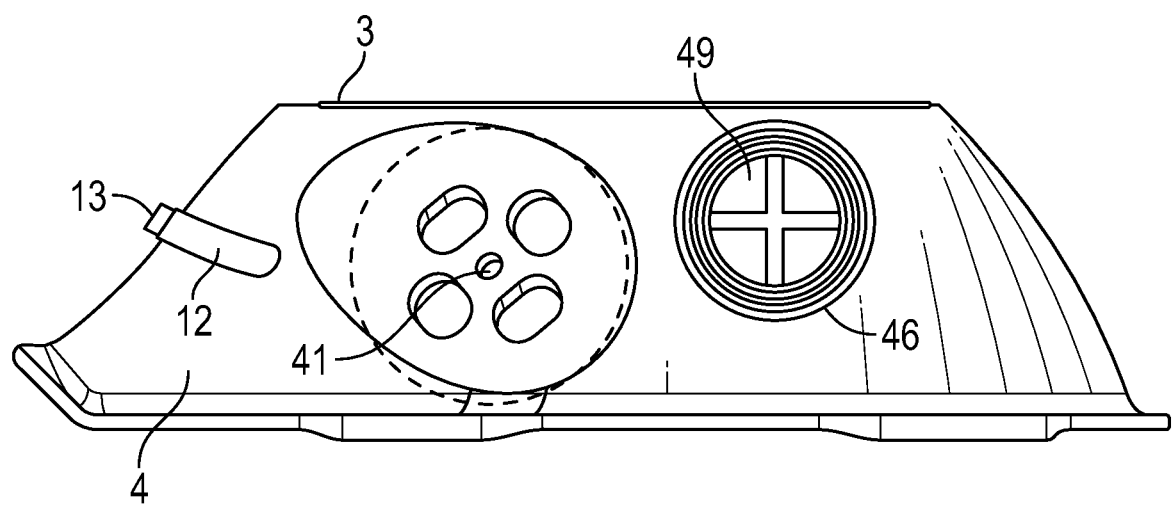
FIG. 3D is a side view of the body of the mask of FIG. 2 in accordance with at least one embodiment described herein.
Figure 3E:
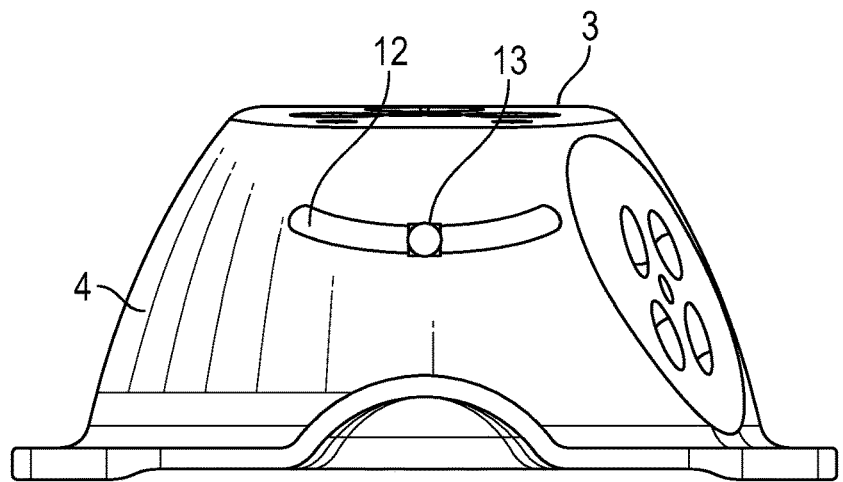
FIG. 3E is an upper end view of the body of the mask of FIG. 2 in accordance with at least one embodiment described herein.
Figure 3F:
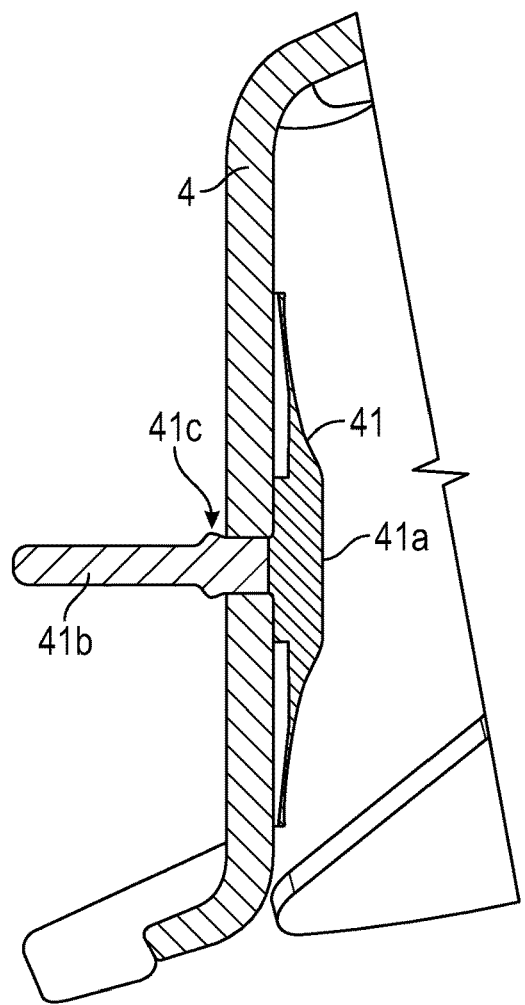
FIG. 3F is a cross-sectional view of an inlet on an outer sidewall of the body of the mask of FIG. 2 in accordance with at least one embodiment described herein.

As specifically depicted in FIG. 3F, in some embodiments, the umbrella valve 41 may include a valve stem 41b extending from a valve skirt 41a, and a valve ball 41c located on the valve stem 41b and spaced from the valve skirt 41a. The valve skirt 41a is configured to reside on an inside surface of the outer sidewall 4 of the body 2 while the valve stem 41b is passed though the outer sidewall 4 with the outer sidewall positioned between the valve skirt 41a and the valve ball 41c. The umbrella valve 41 secured to the sidewall 4 in a manner which allows the valve 41 to move between the open and closed positions.

In some embodiments, the umbrella valve 41 does not filter the air passing therethrough. However, in such embodiments, the mask 1 may be used on a patient located in a sterile room or under sterile conditions wherein the air passing therethrough is generally purified and/or sterilized prior to passing through the umbrella valve 41.

In some embodiments, as further shown in FIGS. 3A, 3C, and 3D, the outlet 45 may be include a filter passage 46 attached thereto. The filter passage 46 may include a fixed end 46a and an opposite free end 46b. The fixed end 46a is attached to and extends away from the outer sidewall 4 around an opening 49 defined therethrough to connect the filter passage 46 to the space 5 within the mask 1. Any portion of the filter passage 46 may include a filter therein. Alternatively, in some embodiments, the filter passage 46 may be free of a filter and the free end 46b of the filter passage 46 may be configured to attach to a separate filter including its own housing and configured to be removably positioned thereon (See FIG. 2).

The mask 1 (and/or body 2) may further include a nose-bridge 12 secured to the body 2 via bridge post 13 extending from outer sidewall 4. The nose-bridge 12 is a thin strip of material, such as a metal, like aluminum, configured to be bent or flexed in order to match a curvature of a patient's nose thereby pinching a portion of the body extending across the nose of the patient to the bridge of the patient's nose. Any suitable node-bridge 12 may be added to the mask 1.

In some embodiments, at least the outer sidewall 4 of the mask 1 is formed using any suitable molding process and the bridge post 13 may be molded with the outer sidewall 4. In such embodiments, the nose-bridge 12 may include a bridge aperture 14 configured to be attached to the sidewall 4 via the post 13 passing through the bridge aperture 14.

As shown in FIGS. 2 and 3A, in some embodiments, the central face 3 of the body 2 may be egg-shaped with the narrower end being on the nasal upper portion 7 of the central face 3. However, the central face may define other suitable shapes including circular, triangular, octagonal, and the like.

Turning now to FIGS. 4A-4G, which depict the various ports (e.g., endoscope ports and/or surgical instrument ports) described herein positioned on the central face 3. The other portions of the mask 1 and/or body 2, including for example, the outer sidewall 4 and various elements associated therewith, are not shown for clarity purposes.

Figure 4A:
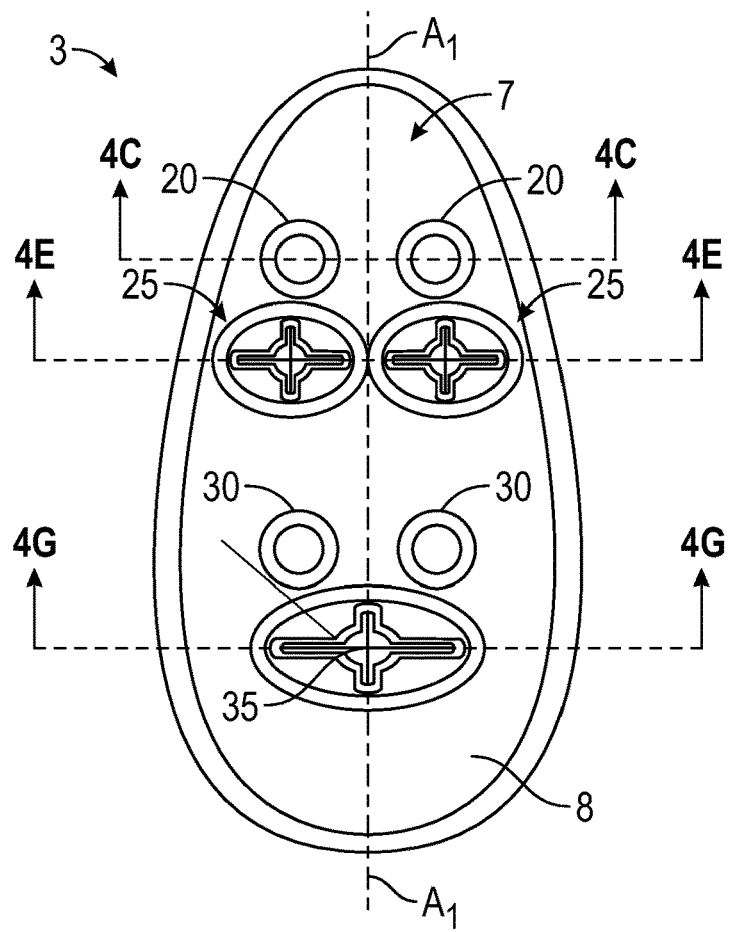
FIG. 4A is a top view of a central face of a body of a patient mask in accordance with at least one embodiment described herein.
Figure 4B:
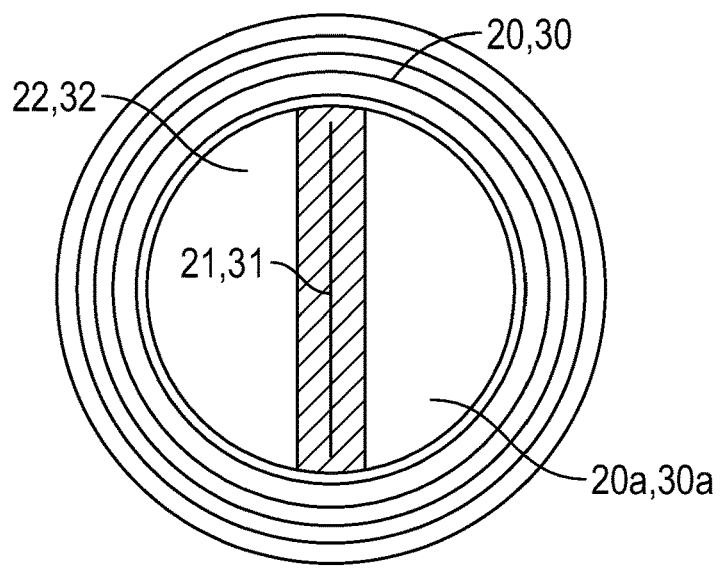
FIG. 4B is a bottom view of an endoscope port of a patient mask in accordance with at least one embodiment herein.
Figure 4C:
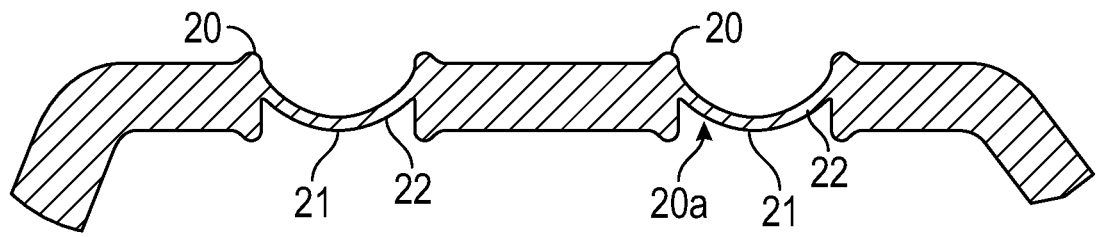
FIG. 4C is a cross-sectional view of the central face of FIG. 4A along D-D.

Initially, as shown in FIGS. 4A-4C the endoscope ports (e.g., the nasal endoscope port 20 and/or the perioral endoscope port 30) described herein may define a generally circular outer perimeter on the face 3 and/or body 2 of the mask 1. In some embodiments, the outer perimeter of the nasal endoscope port 20 being generally the same as the outer perimeter of the perioral endoscope port 30. The endoscope ports 20, 30 may also include an endoscope slit 21, 31 extending across at least a portion of, if not a majority or entirely of, a face of the port 20, 30. In some embodiments, the endoscope slit 21, 31 extends along at least an inner face 20a, 30a of the port 20, 30. In some embodiments, the endoscope slit 21, 31 may be perforated and intended to open when an endoscope is positioned through the port 20, 30. In some embodiments, the endoscope slit 21, 31 extends completely through the thickness of the port 20, 30.

As shown in cross-section in FIG. 4C, the endoscope ports described herein may also include a curved endoscope port wall. Although the cross-section is specifically depicted across the nasal endoscope ports 20, the following description of the nasal endoscope ports 20 in cross section applies equally to the perioral endoscope ports 30.

The nasal endoscope ports 20 include a curved nasal endoscope port wall 22. A thickness of the curved nasal endoscope port wall 22 is less than half a thickness of the central face 3. The curved nasal endoscope port wall 22 is designed to spread pressure from inside the mask 1 equally along the curved or rounded surface of the wall 22 causing the slit 21 to remain self-sealed or closed when a patient exhales and/or provides other nasal/oral expulsions, commonly associated with sneezing, coughing, burping, hiccups, etc.

Turning now to FIGS. 4D-4G, the instrument ports (e.g., the nasal instrument port 25 and/or the perioral instrument port 35) described herein are depicted in more detail. The instrument ports 25, 35 may define a generally elliptical perimeter. The perimeter and/or surface area of the nasal instrument port 25 being generally smaller than the perimeter and/or surface area, respectively of the perioral instrument port 35. In some embodiments, the perimeter and/or the surface area of the perioral instrument port 35 is generally 1.1 to 2.0 times greater than the perimeter and/or surface area, respectively, of the nasal instrument port 25.

Figure 4D:
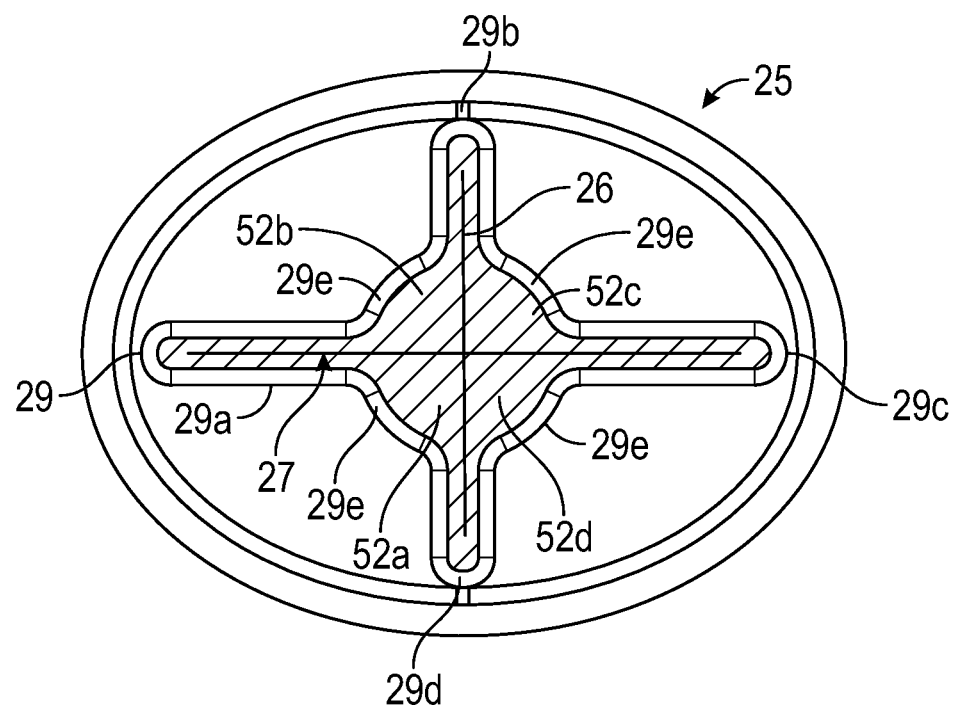
FIG. 4D is a top view of a nasal instrument port of a patient mask in accordance with at least one embodiment herein.
Figure 4E:
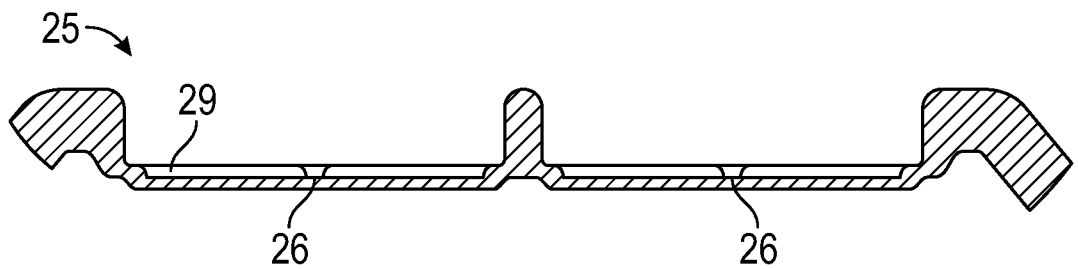
FIG. 4E is a cross-sectional view of the central face of FIG. 4A along E-E.

In FIGS. 4D-4E the nasal instrument ports 25 described herein include first and second nasal instrument slits 26, 27 transverse to each other and crossing each other at a central portion of each slit 26, 27. The first and second nasal slits 26, 27 are defined through the thinnest portion of the linear nasal instrument port wall 28. In some embodiments, the first slit 26 extends generally parallel to the central longitudinal axis A1 of the central face 3 and/or body 2 and the second slit 27 extends perpendicular to the first slit 26. In some embodiments, the first slit 26 is shorter in length than the a length of the second slit 27.

A first recessed inner edge 29 surrounds and/or frames the first and second nasal instrument slits 26, 27. The recessed inner edge 29 is spaced from the first and second nasal instrument slits 26, 27 and confined within an outer perimeter of the port 25. An outer area of the port 25 is positioned between the outer perimeter of the port 25 and the recessed inner edge 29 and represents the thickest portion of the linear nasal instrument port 28. An inner area of the port 25 is positioned between the recessed inner edge 29 and the first and second slits 26, 27 and represents the thinnest portion of the nasal instrument port 28.

The recessed inner edge 29 defines a generally t-shaped and/or telescopic-sight shaped configuration including four generally linear outer arms 29a-d, each arm 29a-d extending from an expanded generally circular central portion 29e. The generally circular central portion 29d of recessed inner edge 29 is spaced farther from the first and second slits 26, 27 than the linear outer arms 29a-d thereby creating flap portions 52 which are thinner than the thicker outer area of the instrument port 25. The flap portions 52 are configured to improve the sealability and/or closing of the instrument port 25 when an instrument is positioned therethrough because the flap portions 52 are sufficiently flexible to wrap around outside of the surgical instrument passing through the nasal instrument port 25. Some non-limiting examples of useful surgical instruments may include tongue depressors, thermometers, swabs, water picks, biopsy tools, ablation devices, cauterizing devices, surgical cutters, surgical fasteners, balloons, and the like.

Figure 4F:
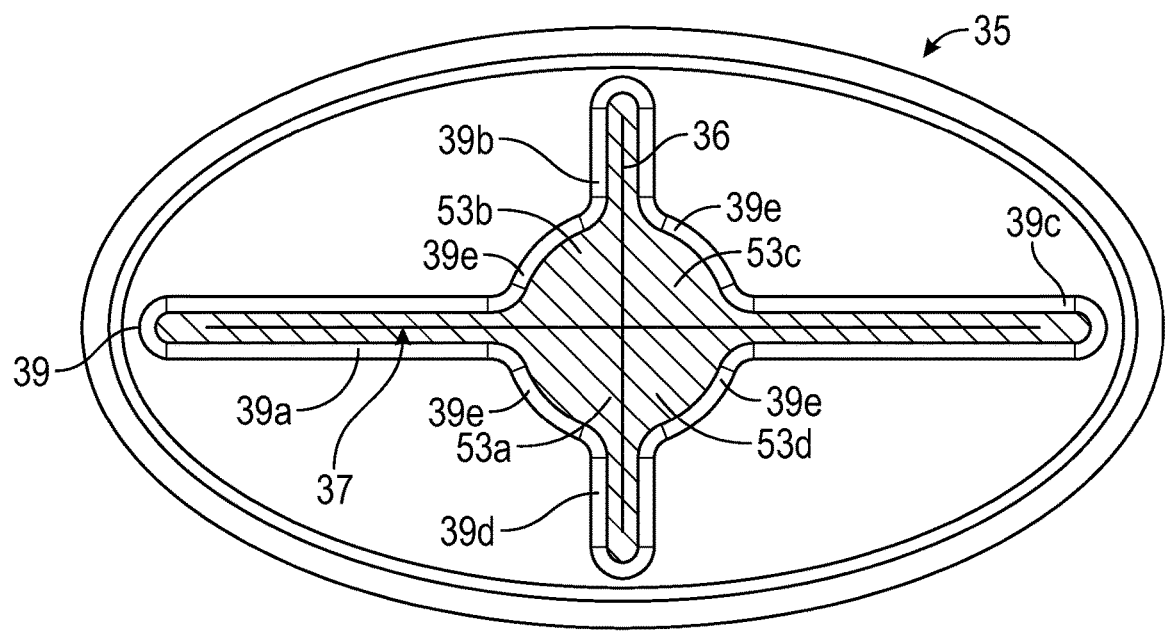
FIG. 4F is a top view of a perioral instrument port of a patient mask in accordance with at least one embodiment herein.
Figure 4G:
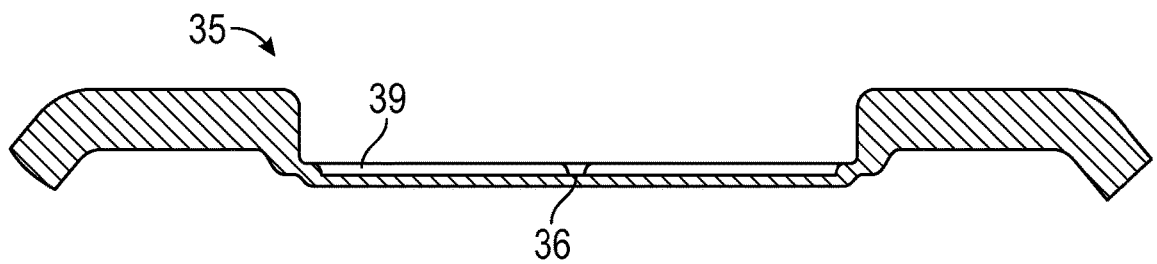
FIG. 4G is a cross-sectional view of the central face of FIG. 4A along F-F.

In FIGS. 4F-4G the perioral instrument ports 35 described herein include first and second perioral instrument slits 36, 37 transverse to each other and crossing each other at a central portion of each slit 36, 37. The first and second perioral slits 36, 37 are defined through the thinnest portion of the linear perioral instrument port wall 38. In some embodiments, the first slit 36 extends generally parallel to the central longitudinal axis A1 of the central face 3 and/or body 2 and the second slit 37 extends perpendicular to the first slit 36. In some embodiments, the first slit 36 is shorter in length than the a length of the second slit 37.

A second recessed inner edge 39 surrounds and/or frames the first and second perioral instrument slits 36, 37. The recessed inner edge 39 is spaced from the first and second perioral instrument slits 36, 37 and confined within an outer perimeter of the port 35. An outer area of the port 35 is positioned between the outer perimeter of the port 35 and the recessed inner edge 39 and represents the thickest portion of the linear perioral instrument port wall 38. An inner area of the port 35 is positioned between the second recessed inner edge 39 and the first and second slits 36, 37 and represents the thinnest portion of the linear perioral instrument port 38.

The second recessed inner edge 39 defines a generally t-shaped and/or telescopic-sight shaped configuration including four generally linear outer arms 39a-d, each arm 39a-d extending from an expanded generally circular central portion 39e. The generally circular central portion 39e of recessed inner edge 39 is spaced farther from the first and second slits 36, 37 than the linear outer arms 39a-d thereby creating instrument flap portions 53a-d which are thinner than the thicker outer area of the instrument port 35. The instrument flap portions 53 are configured to improve the sealability and/or closing of the instrument port 35 when an instrument is positioned therethrough because the flap portions 53a-d are sufficiently flexible to wrap around outside of the surgical instrument passing through the perioral instrument port 35. Some non-limiting examples of useful surgical instruments may include tongue depressors, swabs, thermometers, water picks, biopsy tools, ablation devices, cauterizing devices, surgical cutters, surgical fasteners, balloons, and the like.

In some embodiments, the body 2 of the patient masks 1 described herein may be generally of one-piece construction, and particularly, the central face 3, the outer sidewall 4, and the sidewall ledge 9 may be generally of one-piece construction (See FIGS. 2-3F). In particular embodiments, the body 2 of the patient masks 1 described herein may be generally a molded one-piece of construction.

In some embodiments, as shown in FIGS. 5A-5D, the body 102 of the mask 101 described herein may be made of multiple pieces, and particularly, the central face 103 may be formed separately from the outer sidewall 104 and/or the sidewall ledge 109. Unless otherwise provided, the body 102 of the mask 101 (including a central face 103, outer sidewall 104, and/or ledge 109) of FIGS. 5A-5D is generally similar to the body 2 of the mask 1 (including a central face 3, outer sidewall 4, and/or ledge 9) depicted in FIGS. 2-3E and may further include any combination of other additional elements associated therewith.

As illustrated in FIG. 5A, the patient mask 101 may include a body 102 including an outer sidewall 104 having a first peripheral sidewall edge 104a defining a body aperture 117 configured to receive a separate central face 103 therein. As further depicted, in some embodiments, the first peripheral sidewall edge 104a may include a body groove 118 designed to receive and/or at least temporarily maintain, a peripheral ledge 103c of the central face 103 therein to secure the central face 103 to the body 102 of the mask 101. It is envisioned that in some embodiments, the central face may simply be snapped into place in the body aperture. It is further envisioned that in some other embodiments, the central face and the body may include any suitable combination of complimentary male/female locking members to attach the central face to the body.

In such multipiece embodiments, as illustrated in FIGS. 5A-5D, the body 102 may be configured to receive a variety of different central faces 103 having different combinations of endoscope ports 120, 130 and/or instrument ports 125, 135. For example, in some embodiments, the central face 103 may include more than one, such as two, nasal endoscope ports 120, one nasal instrument port 125, more than one, such as two, perioral endoscope ports 130, and one perioral instrument port 135 (FIG. 5B). In some embodiments, the central face 103 may include only nasal ports 120, 125, such as one or more nasal endoscope ports 120 and/or one or more nasal instrument ports 125 (FIG. 5C). In still other embodiments, the central face 103 may include only perioral ports 130, 135, such as one or more perioral endoscope ports 130 and/or one or more perioral instrument ports 135 (FIG. 5D).

Figure 6A:
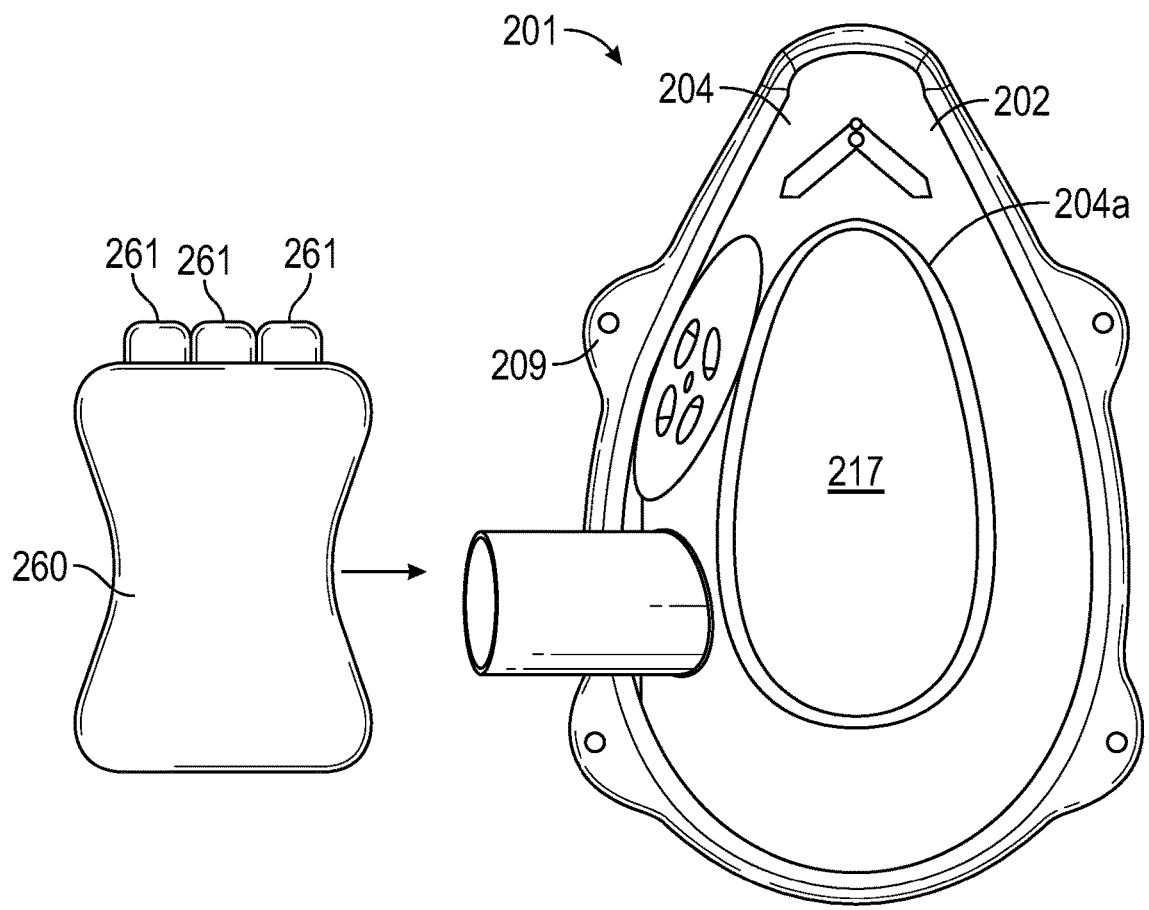
FIG. 6A is a side and top view of a multipiece body of a patient mask in accordance with at least one embodiment herein.
Figure 6B:
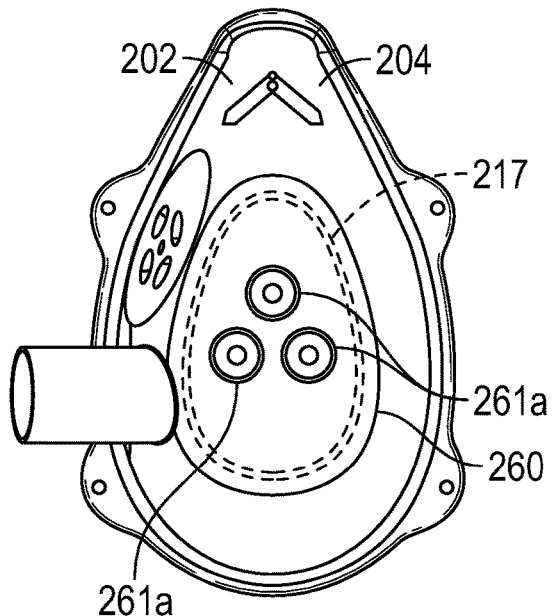
FIG. 6B is a top view of multipiece body of a patient mask in accordance with at least one embodiment herein.
Figure 6C:
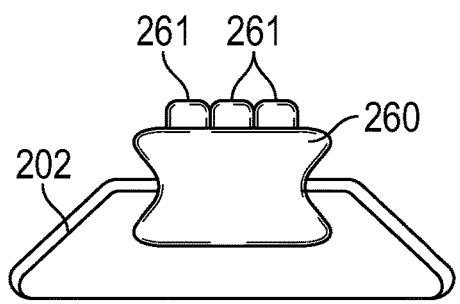
FIG. 6C is a cross-sectional side view of the multipiece body of the mask of FIG. 6B in accordance with at least one embodiment herein.

In some embodiments, as shown in FIGS. 6A-6C, the body 202 of the mask 201 described herein may be configured to interact with a separate access port 260 instead of a central face. Unless otherwise provided, the body 202 of the mask 201 (including an outer sidewall 204, and/or ledge 209) of FIGS. 6A-6C is generally similar to the body 2, 102 of the mask 1, 101 (including an outer sidewall 4, 104 and/or ledge 9, 109) depicted in FIGS. 2-3E and 5A-5D and may further include any combination of other additional elements associated therewith.

As depicted in FIGS. 6A-6C, in some embodiments, the body 202 may be configured to receive an access port 260 within the body aperture 217 defined by the first peripheral sidewall 204a. For example, the access port 260 may be a flexible access port such as a SILS™ port (Covidien) designed to be readily deformable to be received within the body aperture 217 and readily expandable after deformation to fill and seal the body aperture 217 following placement therein. The access port 260 includes multiple preformed ports 261 configured to receive various combinations of endoscopes and/or surgical instruments as needed.

Figure 7:
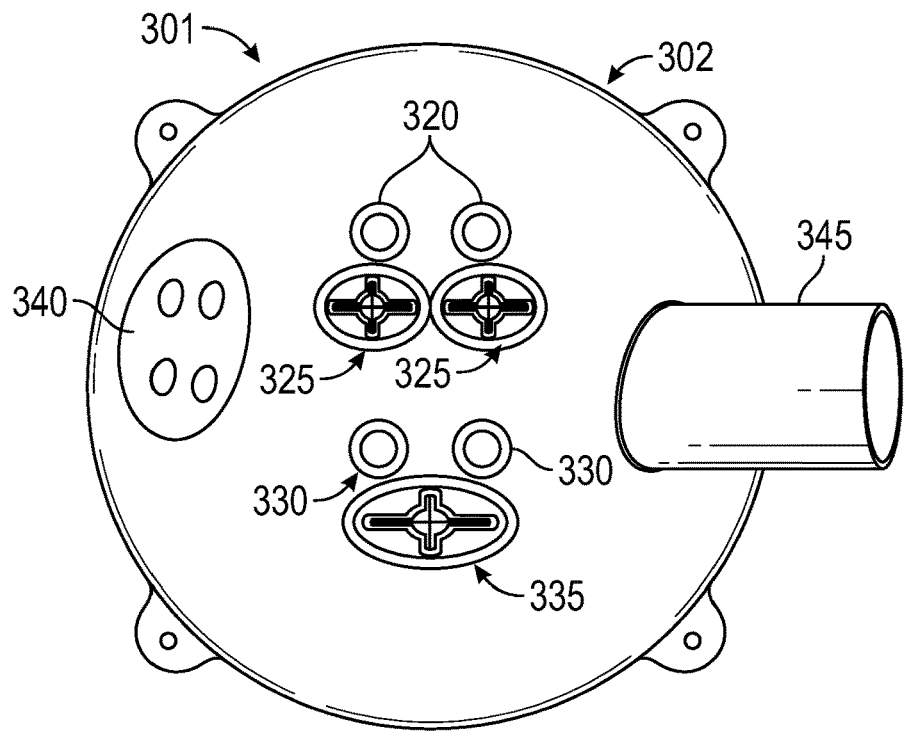
FIGS. 7-9 are each a top view of a body of a patient mask in accordance with at least one embodiment herein.

Turning now to FIG. 7, in some embodiments, the mask 301 includes a generally domed one-piece body 302. The body 302 may be generally circular shaped. The body 302 includes any combination of endoscope ports and/or instrument ports as described herein. In some embodiments, the body 302 includes any combination of one or more nasal endoscope ports 320, one or more nasal instrument ports 325, one or more perioral endoscope ports 330, and/or one or more perioral instrument ports 335. In addition, in some embodiments, the inlet 340 and outlet 345 as described herein may be positioned on opposite sides of the body 302. Although not shown for clarity purposes, any of the parts of the mask 1, 101 and/or body 2, 102 described hereinabove may be included in the mask 301 and/or body 302 of FIG. 7, such as straps, nose-bridge, outer ledge, etc.

Figure 8:
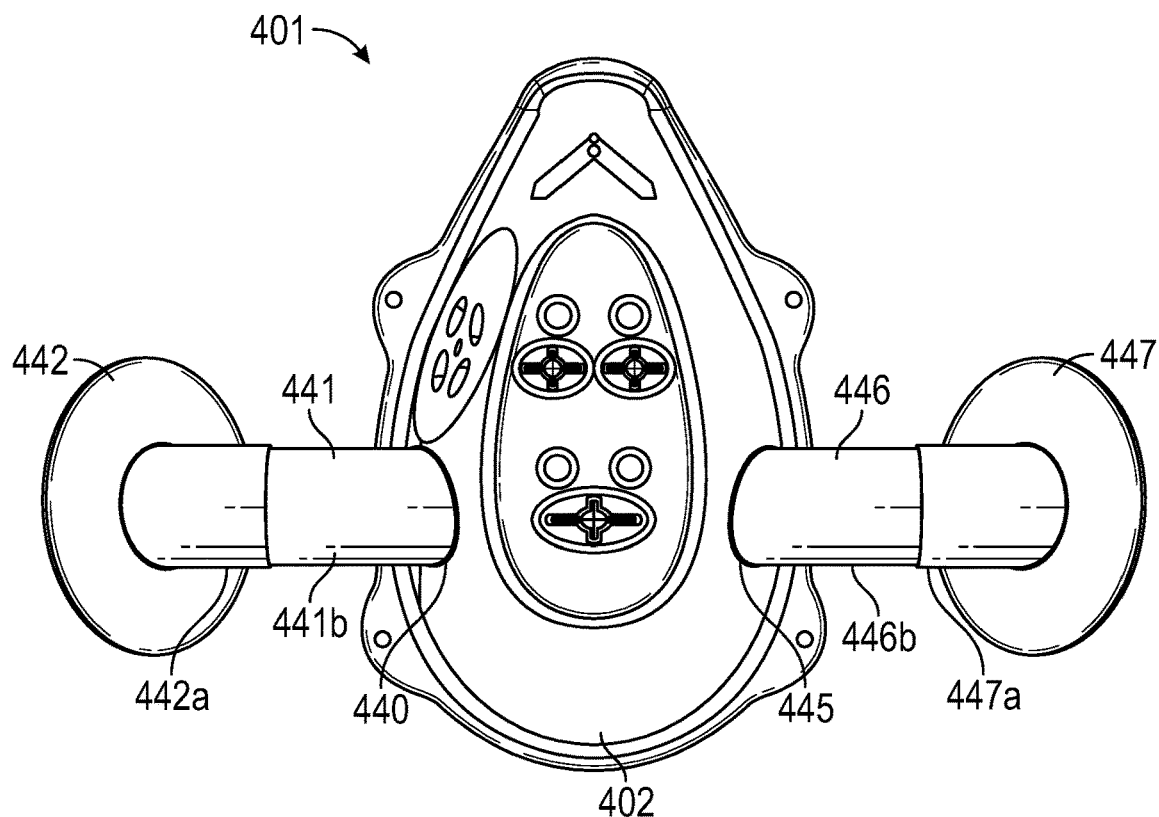
Figure 9:
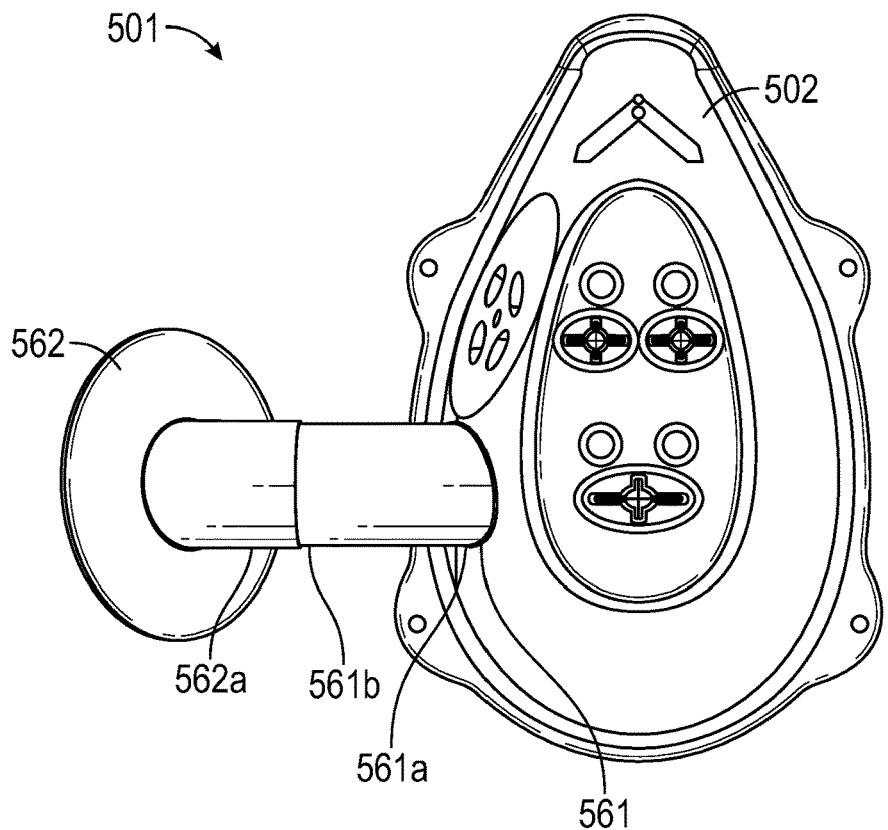

In some embodiments, as shown in FIGS. 8 and 9, a patient mask 401, which may be generally similar to any of the masks 1, 101, 201, 301 described herein, may include an inlet 440 which is not an umbrella valve.

As shown in FIG. 8, in some embodiments, the mask 401 may include an inlet 440 and an outlet 445 positioned on opposite side of the body 402 which include a first filter passage 441 and a second filter passage 446, respectively. In some embodiments, at least one of, if not both, the first or second filter passages 441, 446 may include a one-way filter configured to purify and/or sterilize the air passing therethrough. For example, in some embodiments, at least the first filter passage 441 further includes and/or is attached to a first one-way filter 442 designed to filter the air passing from outside the mask 401 (and/or body 402) through the first filter 442 and into the space inside the mask 401 (and/or body 402).

In some embodiments, the first one-way filter 442 is separate from the body 402 but includes a first end 442a configured to attach to the body 402 and/or a free end 441b of the filter passage 441 opposite the attached end 441a. The first filter 442 also includes a free end configured to receive an adapter for attaching to an endotracheal tube thereto (not shown). In some embodiments, the first filter 442 may be configured as an angled first filter that extends from the body 402 at an angle to generally wrap around one side of the patient's face, as opposed to extending along and/or across the patient's face like the body 402. Any suitable one-way filter may be used. In some embodiments, the one-way first filter 442 may be a DART™ Filter (Covidien).

As further shown in FIG. 8, in some embodiments, at least the second filter passage 446 further includes and/or is attached to a second one-way filter 447 designed to filter the air passing from the space inside the mask 401 (and/or body 402) through the second filter 447 to outside the mask 401 (and/or body 402). In some embodiments, the second one-way filter 447 is separate from the body 402 but includes a first end 447a configured to attach to the body 402 and/or a free end 446b of the second filter passage 446 opposite the attached end 446a. The second filter 447 also includes a free end 447b configured to receive an adapter configured to attach an endotracheal tube thereto (not shown). In some embodiments, the second filter 447 may be configured as an angled second filter that extends from the body 402 at an angle to generally wrap around a second side of the patient's face, as opposed to extending along and/or across the patient's face like the body 402. Any suitable one-way filter may be used. In some embodiments, the one-way second filter 447 may be a DART™ Filter (Covidien).

As shown in FIG. 9, in some embodiments, the mask 501 may include only one filter passage 561 attached to the body 502 which includes a two-way filter 562 configured to purify and/or sterilize the air passing therethrough in both directions. In some embodiments, the two-way filter 562 is separate from the body 502 but includes a first end 562a configured to attach to the body 502 and/or a free end 561b of the filter passage 561 opposite the attached end 561a. In some embodiments, the filter 562 may be configured as an angled two-way filter that extends from the body 502 at an angle to generally wrap around one side of the patient's face, as opposed to extending along and/or across the patient's face like the body 502. Any suitable two-way filter may be used.

Figure 10:
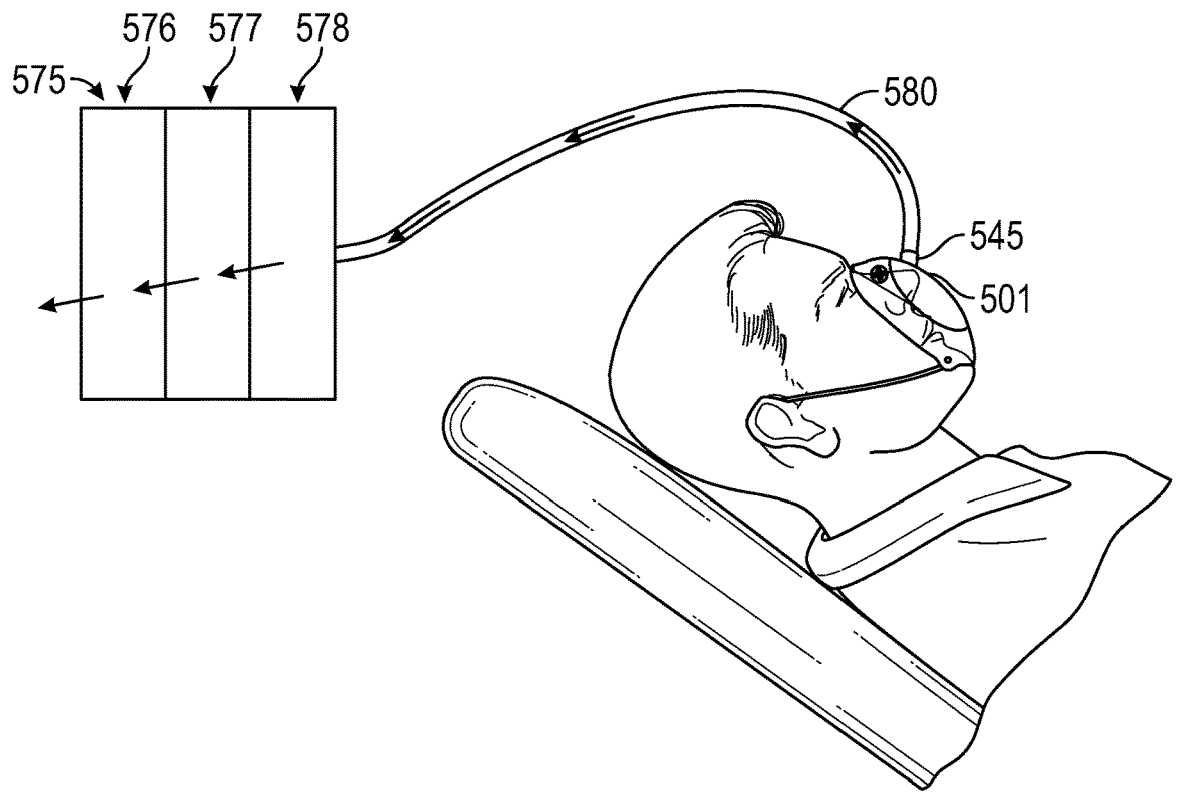
FIG. 10 is a schematic view of a patient mask and system associated therewith in accordance with at least one embodiment herein.

In some embodiments, rather than including the one or more filters described herein, the masks described herein may alternatively include an outlet configured to attach directly to a separate free-standing air purification and/or filtration system. For example, as shown in FIG. 10, a patient mask 501, which may be generally similar to any of the masks 1, 101, 201, 301 described herein, may include an outlet 545 connected to a separate free-standing air purification and/or filtration system 575. A disposable tube 580 may attach the outlet 545 of the mask 501 to the system 575.

The system 575 includes an evacuator 576 and at least one of a HEPA filter 577, an ultraviolet (UV) light source 578, or both. The evacuator 576 is employed to direct airflow of the patient's exhalation. The evacuator 576 includes an evacuation pump that generates a negative air-pressure which draws the air from inside the mask 501 to the system 575, and particularly from inside the mask 501 through the outlet 545 and the disposable tube 580 before being passed through the HEPA filter 577 and/or UV light source 578 which sterilizes and/or purifies the air and removes any particles, viruses, bacteria, and other contaminants from the patient's exhaled air. After processing through the system, the air may be safely released back into the operating room and/or vented out beyond the operating room and/or hospital.

In addition, by creating a negative pressure inside the mask 501, air from the operating room may be more easily passed through an inlet into the mask and ultimately drawn into the evacuator, as well. This may help to ensure that other particles, virus, bacteria, or other contaminants are also treated and/or purified. The evacuation pump is sized such that the negative pressure created is sufficient to draw air, aerosolized particles, aerosolized droplets of water and other bodily fluids into the system.

Figure 11A:
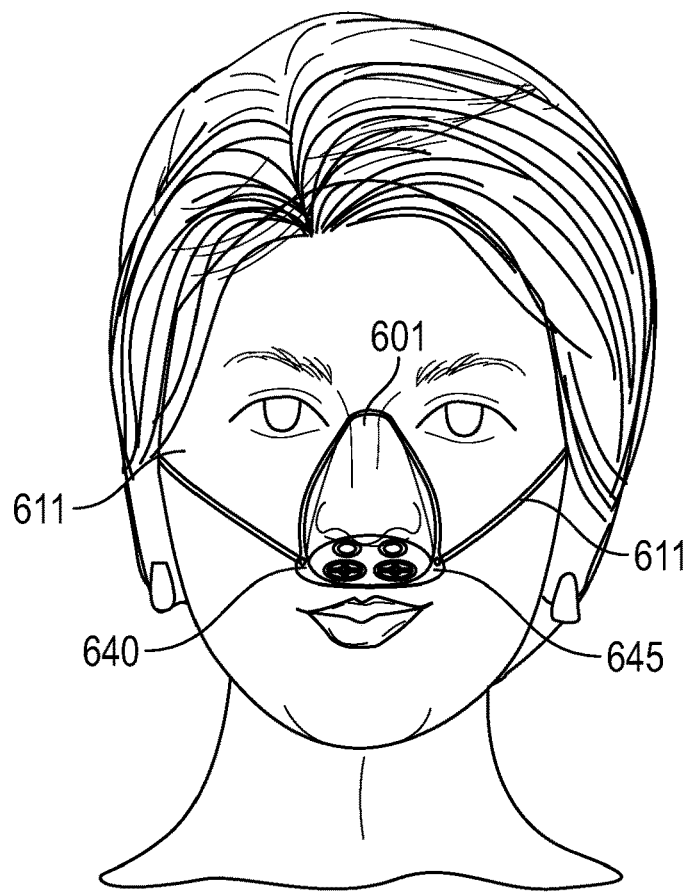
FIG. 11A is a perspective view of a patient mask in accordance with at least one embodiment herein.
Figure 11B:
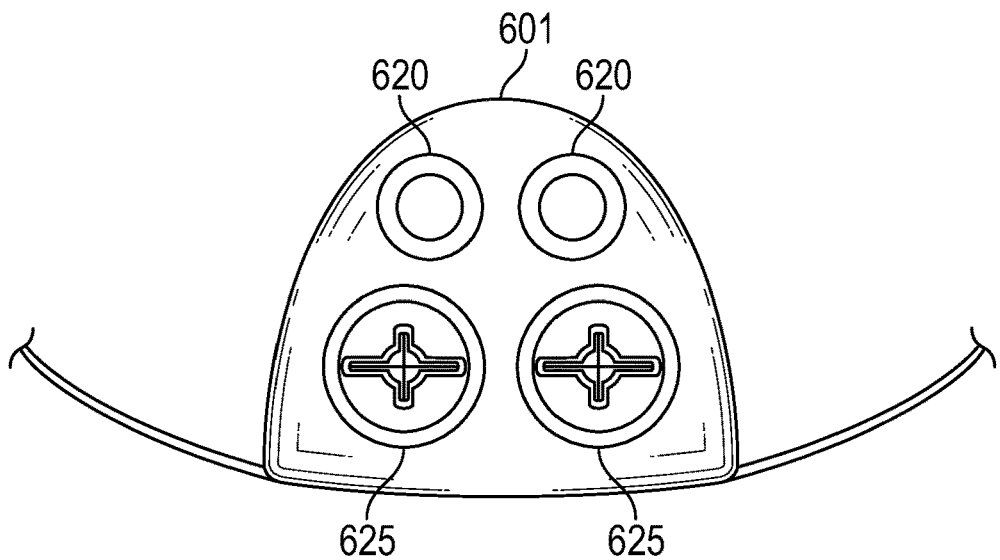
FIG. 11B is a lower end view of the mask of FIG. 11A.

Turning now to FIGS. 11A and 11B, in some embodiments, the patient mask may be only a nasal mask 601 configured to cover only the nose and/or nasal area of a patient. In such embodiments, the nasal patient mask 601 may only include one or more nasal endoscope ports 620, one or more nasal instrument ports 625, or both. The nasal endoscope ports 620 and the nasal instrument ports 625 being generally similar to any of the nasal ports described herein. The mask 601 may also include a nasal inlet 640 and nasal outlet 645. The nasal inlet and nasal outlet being generally similar to any of the inlets and outlets described herein. As shown, in some embodiments, the inlet 640 and outlet 645 are defined along with and/or through the straps 611 extending away from the mask 601. In some embodiments, the straps may be tubular in construction to allow air and/or bodily fluids associated therewith to flow therethrough.

Figure 12:
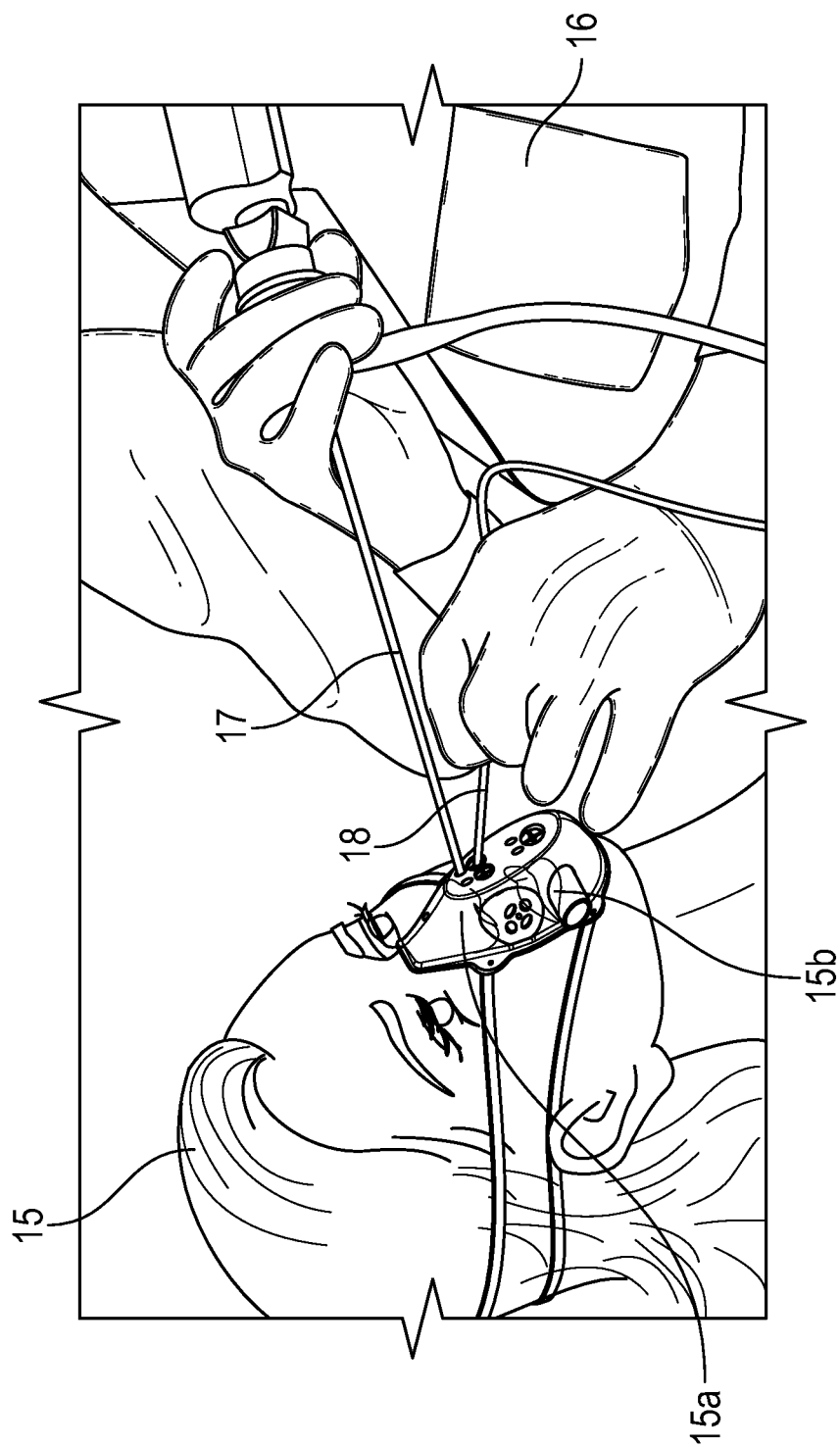
FIG. 12 shows a patient with an endoscope and another surgical instrument inserted through an endoscope port and an instrument port, respectively, of a patient mask as described herein, and into one or more nares of the patient's nose during a typical ENT procedure.

As shown in FIG. 12, in some embodiments, the patient masks described herein are designed to be worn by a patient during a medical procedure, and particular an ENT-related medical procedure. The mask covers both a nasal area 15a and a perioral area 15b of the patient 15. Endoscope 17 is shown inserted through a nasal endoscope port on the mask and into the nose of the patient 15. Surgical instrument 18 is shown inserted through a nasal instrument port on the mask and into the nose pf the patient 15. Any of the filters described herein may be part of and/or further combined with the sealed mask as shown to prevent the transmission of harmful particles, viruses, such as COVID, and/or bacteria from the patient to the clinician via the patient's contaminated exhaled air and/or any other nasal/oral expulsions.

Each of the various masks and/or mask bodies described herein may be made using any suitable method including, but not limited to, molding, pressing, or extruding. In some embodiments, the mask and/or body are made from a molding process.

Each of the various masks and/or mask bodies described herein may be made from any suitable material. In some embodiments, the mask and/or body may be made from a material such as silicone, polypropylene, rubber, polyphenylsulfone, high-density polyethylene (HDPE), acrylonitrile butadiene styrene (ABS), acrylic polymethyl methacrylate (acrylic PMMA), acetal copolymer (POM), polyetheretherketone (PEEK), polybutylene terephthalate, polycarbonate, and combinations thereof.

In some embodiments, the masks and/or mask bodies described herein may be made from silicone. In some embodiments, the silicone may have a greater than 300% elongation at break and/or a durometer range from about 50-70 Shore A hardness.

In some embodiments, the central face of the patient mask may be made from a different material than the outer sidewall of the mask. For example, the central face may be made of a stiffer more durable material, such as silicone, as compared to the outer sidewall which may be made from a softer more flexible and cheaper material such as polypropylene and the like.

Each of the various masks and/or bodies described herein may be made to be sterilizable or non-sterilizable.

In some embodiments, at least a portion, if not the entire mask or body may be transparent For example, in some embodiments, either or both the central face and the outer sidewall of the body may be transparent.

In some embodiments, at least a portion, if not the entire mask or body may be a disposable mask For example, in some embodiments, either or both of the central face and the outer sidewall of the body may be disposable.

Each of the various masks and/or mask bodies described herein may be combined with any combination of the various elements described herein to form a sterile surgical kit. For example, in some embodiments, a surgical kit may include any of the patient masks described herein including a one-piece body and a separate filter configured to be attached thereto during use. Such a surgical kit may further include at least one of an adapter configured to attach an endotracheal tube or suction device to the filter, at least one strap, and/or a disposable tube for attachment to a separate system. In another example, in some embodiments, a surgical kit may include any of the patient masks described herein including a multi-piece body and a separate filter configured to be attached thereto during use. Such a surgical kit may further include at least one of interchangeable central faces of different port design, one or more access ports, such as a SILS™ port (Covidien), an adapter configured to attach an endotracheal tube and/or suction device to the filter, at least one strap, and/or a disposable tube for attachment to a separate system.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A patient mask comprising:
    a body shaped to cover at least a portion of a face of a patient creating a space between the body and the face of the patient, a plurality of removeably engageable central faces configured to cover a nasal area of the patient, the body configured to receive one of the plurality of removeably engageable central faces, the body including a perioral portion configured to cover a perioral area of the patient,
    at least one nasal endoscope port configured to receive an endoscope therethrough, the at least one nasal endoscope port being self-sealing and positioned on an upper nasal portion of each central face of the body,
    at least one nasal instrument port configured to receive a surgical instrument therethrough, the at least one nasal instrument port being self-sealing and positioned on a lower nasal portion of each central face of the body, and
    at least one filter passage attached to the body, the at least one filter passage configured to filter air passing therethrough,
    wherein each central face is selectively engageable with the body to accommodate a variety of different combinations of endoscope port locations, nasal instrument port locations, endoscope port shapes and port sizes or instrument port shapes and port sizes.

2. The patient mask of claim 1, wherein the at least one nasal endoscope port includes a first and second nasal endoscope port and the at least one nasal instrument port includes a first and second nasal instrument port.

3. The patient mask of claim 1, further comprising at least one perioral endoscope port configured to receive an endoscope therethrough, the at least one perioral endoscope port being self-sealing and positioned on a first part of the perioral portion of the body and at least one perioral instrument port configured to receive a surgical instrument therethrough, the at least one perioral instrument port being self-sealing and positioned on a second part of the perioral portion of the body.

4. The patient mask of claim 3, wherein the at least one perioral endoscope port includes a first and second perioral endoscope port and the at least one perioral instrument port includes a first perioral instrument port.

5. The patient mask of claim 1, wherein the at least one filter passage includes a first one-way filter passage configured to filter air passing therethrough from the space inside the body of the mask to outside the body of the mask.

6. The patient mask of claim 5, further comprising a second one-way filter passage configured to filter air passing therethrough from outside the body of the mask into the space inside the body of the mask.

7. The patient mask of claim 5, further comprising an umbrella valve configured to transition between an open position during inhalation of the patient and a closed position during exhalation of the patient, the open position configured to allow air to pass through the valve from outside the body of the mask into the space inside the body of the mask, and the closed position configured to prevent air to pass therethrough.

8. The patient mask of claim 1, wherein the at least one filter passage includes a two-way filter passage configured to filter air passing therethrough in a first direction from the space inside the body of the mask to outside the body of the mask and further configured to filter air passing therethrough in a second direction from outside the body of the mask into the space inside the body of the mask.

9. The patient mask of claim 1, further comprising at least one strap secured to a portion of the body, the at least one strap configured to secure the mask to the face of the patient.

10. The patient mask of claim 1, further comprising a nose-bridge.

11. The patient mask of claim 1, wherein the body is a molded one-piece body.

12. A patient mask comprising:
    a body, a plurality of removeably engageable central faces, the body configured to receive one of the plurality of removeably engageable central faces, the body surrounded by an outer sidewall, the outer sidewall configured to space the central face of the body from a face of a patient, each central face including a nasal portion configured to cover a nasal area of the patient and a perioral portion configured to cover a perioral area of the patient,
    at least one nasal endoscope port configured to receive an endoscope therethrough, the at least one nasal endoscope port being self-sealing and positioned on an upper nasal portion of each central face of the body,
    at least one nasal instrument port configured to receive a surgical instrument therethrough, the at least one nasal instrument port being self-sealing and positioned on a lower nasal portion of each central face of the body, and
    at least one filter passage attached to the body, the at least one filter passage configured to filter air passing therethrough,
    wherein each central face is selectively engageable with the body to accommodate a variety of different combinations of endoscope port locations, nasal instrument port locations, endoscope port shapes and port sizes or instrument port shapes and port sizes.

13. The patient mask of claim 12, wherein the at least one nasal endoscope port includes a first and second nasal endoscope port and the at least one nasal instrument port includes a first and second nasal instrument port.

14. The patient mask of claim 12, further comprising a first and second perioral endoscope port and the at least one perioral instrument port includes a first perioral instrument port.

15. The patient mask of claim 12, wherein the at least one filter passage includes or is attached to a one-way filter passage configured to filter air passing therethrough from the space inside the body of the mask to outside the body of the mask and the mask further comprises an umbrella valve configured to transition between an open position during inhalation of the patient and a closed position during exhalation of the patient, the open position configured to allow air to pass through the valve from outside the body of the mask into the space inside the body of the mask, and the closed position configured to prevent air to pass therethrough.

16. The patient mask of claim 12, wherein the at least one filter passage includes or is attached to a one-way filter passage configured to filter air passing therethrough from the space inside the body of the mask to outside the body of the mask and the mask further comprises a second one-way filter passage configured to filter air passing therethrough from outside the body of the mask into the space inside the body of the mask.

17. The patient mask of claim 12, wherein the at least one filter passage includes a two-way filter passage configured to filter air passing therethrough in a first direction from the space inside the body of the mask to outside the body of the mask and configured to filter air passing therethrough in a second direction from outside the body of the mask into the space inside the body of the mask.

18. The patient mask of claim 12, wherein the at least one filter passage is connected to a separate air filtration system via a disposable tube.

19. The patient mask of claim 12, wherein the body is a multi-piece body including a first piece including the outer sidewall and a second piece including the central face, wherein the central face is configured to attach to a second end portion of the outer sidewall opposite the face of the patient.

20. A kit comprising:
a patient mask including,
a body, a plurality of removeably engageable central faces, the body configured to receive one of the plurality of removeably engageable central faces, the body surrounded by an outer sidewall, the outer sidewall configured to space each central face of the body from a face of a patient, each central face including a nasal portion configured to cover a nasal area of the patient and a perioral portion configured to cover a perioral area of the patient,
at least one nasal endoscope port configured to receive an endoscope therethrough, the at least one nasal endoscope port being self-sealing and positioned on an upper nasal portion of each central face of the body,
at least one nasal instrument port configured to receive a surgical instrument therethrough, the at least one nasal instrument port being self-sealing and positioned on a lower nasal portion of each central face of the body; and
at least one filter configured to attach to the sidewall of the body at an angle, and
an endotracheal tube adapter configured to selectively attach an endotracheal tube to a free end of the filter,
wherein each central face is selectively engageable with the body to accommodate a variety of different combinations of endoscope port locations, nasal instrument port locations, endoscope port shapes and port sizes or instrument port shapes and port sizes.

* * * * *